(12) United States Patent
Khosravi et al.

(10) Patent No.: US 8,092,514 B1
(45) Date of Patent: Jan. 10, 2012

(54) STRETCHABLE ANTI-BUCKLING COILED-SHEET STENT

(75) Inventors: Farhad Khosravi, San Mateo, CA (US); Himanshu N. Patel, San Jose, CA (US); Yi Yang, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 873 days.

(21) Appl. No.: 09/427,260

(22) Filed: Oct. 25, 1999

Related U.S. Application Data

(63) Continuation-in-part of application No. 09/192,977, filed on Nov. 16, 1998, now Pat. No. 6,325,820.

(51) Int. Cl.
 *A61F 2/06* (2006.01)
(52) U.S. Cl. .................... 623/1.15; 623/1.19
(58) Field of Classification Search ............. 623/1.15, 623/1.18, 1.19, 1.21, 23.7, 901, 1.2, 1.44, 623/1.37; 606/191, 194, 198
See application file for complete search history.

(56) References Cited

U.S. PATENT DOCUMENTS

| | | |
|---|---|---|
| 3,868,956 A | 3/1975 | Alfidi et al. |
| 4,503,569 A | 3/1985 | Dotter |
| 4,512,338 A | 4/1985 | Balko et al. |
| 4,565,589 A | 1/1986 | Harrison |
| 4,631,094 A | 12/1986 | Simpson et al. |
| 4,795,458 A | 1/1989 | Regan |
| 4,830,003 A | 5/1989 | Wolff et al. |
| 4,950,227 A | 8/1990 | Savin et al. |
| 4,994,071 A | 2/1991 | MacGregor |
| 5,019,085 A | 5/1991 | Hillstead |
| 5,035,706 A | 7/1991 | Giantureo et al. |
| 5,037,427 A | 8/1991 | Harada et al. |
| 5,089,005 A | 2/1992 | Harada |
| 5,100,429 A | 3/1992 | Sinofsky et al. |
| 5,135,536 A | 8/1992 | Hillstead |
| 5,158,548 A | 10/1992 | Lau et al. |

(Continued)

FOREIGN PATENT DOCUMENTS
DE 19834956 A1 5/1999

(Continued)

OTHER PUBLICATIONS

F. Khosravi, et al., PCT Publication No. WO 99/48441, "Coiled Sheet Graft for Single and Bifurcated Lumens and Methods of Makng and Use", Sep. 30, 1999.

(Continued)

*Primary Examiner* — Brian E. Pellegrino
(74) *Attorney, Agent, or Firm* — Vidas, Arrett & Steinkraus, P.A.

(57) ABSTRACT

A stent includes a coiled-up sheet having overlapping inner and outer longitudinal sections extending parallel to a longitudinal axis thereof, and defining a periphery, the coiled-up sheet being unrollable between contracted and enlarged conditions. A plurality of stretchable elements are formed in the coiled-up sheet, the stretchable elements being expandable about the periphery between an unstretched condition to facilitate placement in a delivery device in the contracted condition and a stretched condition to facilitate expansion of the coiled-up sheet to the enlarged condition upon deployment from the delivery device. Preferably, the coiled-up sheet is biased to the enlarged condition, and the stretchable elements are biased to the stretched condition. More preferably, at least one of the biases is provided by a shape memory property of the coiled-up sheet, which is activated by exposing the stent to body temperature.

9 Claims, 18 Drawing Sheets

U.S. PATENT DOCUMENTS

| | | | | |
|---|---|---|---|---|
| 5,167,614 A | * | 12/1992 | Tessmann et al. | 623/1.15 |
| 5,197,978 A | | 3/1993 | Hess | |
| 5,282,824 A | | 2/1994 | Gianturco | |
| 5,330,500 A | | 7/1994 | Song | |
| 5,354,308 A | | 10/1994 | Simon et al. | |
| 5,356,423 A | | 10/1994 | Tihon et al. | |
| 5,395,390 A | | 3/1995 | Simon et al. | |
| 5,405,377 A | | 4/1995 | Cragg | |
| 5,441,515 A | * | 8/1995 | Khosravi et al. | 606/194 |
| 5,443,498 A | | 8/1995 | Fontaine | |
| 5,443,500 A | | 8/1995 | Sigwart | |
| 5,449,373 A | | 9/1995 | Pinchasik et al. | |
| 5,466,242 A | | 11/1995 | Mori | |
| 5,197,978 A | | 5/1996 | Hess | |
| 5,540,712 A | | 7/1996 | Kleshinski et al. | |
| 5,556,413 A | | 9/1996 | Lam | |
| 5,562,641 A | | 10/1996 | Flomenblit et al. | |
| 5,597,378 A | | 1/1997 | Jervis | |
| 5,618,299 A | | 4/1997 | Khosravi et al. | |
| 5,624,508 A | | 4/1997 | Flomenblit et al. | |
| 5,649,952 A | | 7/1997 | Lam | |
| 5,649,977 A | | 7/1997 | Campbell | |
| 5,665,115 A | | 9/1997 | Cragg | |
| 5,728,150 A | | 3/1998 | McDonald et al. | |
| 5,733,303 A | | 3/1998 | Israel et al. | |
| 5,733,330 A | | 3/1998 | Cox | |
| 5,746,765 A | | 5/1998 | Kleshinski et al. | |
| 5,755,734 A | | 5/1998 | Richter et al. | |
| 5,766,237 A | | 6/1998 | Cragg | |
| 5,788,979 A | | 8/1998 | Alt et al. | |
| 5,800,520 A | * | 9/1998 | Fogarty et al. | 623/1.37 |
| 5,807,404 A | | 9/1998 | Richter | |
| 5,824,045 A | | 10/1998 | Alt | |
| 5,824,052 A | * | 10/1998 | Khosravi et al. | 623/1.35 |
| 5,824,054 A | | 10/1998 | Khosravi et al. | |
| 5,833,707 A | | 11/1998 | McIntyre et al. | |
| 5,836,964 A | | 11/1998 | Richter et al. | |
| 5,843,117 A | | 12/1998 | Alt et al. | |
| 5,843,120 A | | 12/1998 | Israel et al. | |
| 5,843,175 A | | 12/1998 | Frantzen | |
| 5,843,176 A | | 12/1998 | Weier | |
| 5,855,600 A | | 1/1999 | Alt | |
| 5,860,999 A | | 1/1999 | Schnepp-Pesch et al. | |
| 5,868,782 A | | 2/1999 | Frantzen | |
| 5,871,437 A | | 2/1999 | Alt | |
| 5,876,434 A | | 3/1999 | Flomenblit et al. | |
| 5,882,444 A | | 3/1999 | Flomenblit et al. | |
| 5,895,406 A | * | 4/1999 | Gray et al. | 606/198 |
| 5,902,317 A | | 5/1999 | Kleshinski et al. | |
| 5,954,743 A | * | 9/1999 | Jang | 623/1.15 |
| 5,964,770 A | | 10/1999 | Flomenblit et al. | |
| 5,976,182 A | | 11/1999 | Cox | |
| 6,007,573 A | | 12/1999 | Wallace et al. | |
| 6,015,433 A | | 1/2000 | Roth | |
| 6,042,605 A | * | 3/2000 | Martin et al. | 623/1.5 |
| 6,048,360 A | | 4/2000 | Khosravi et al. | |
| 6,086,610 A | * | 7/2000 | Duerig et al. | 623/1.18 |
| 6,290,720 B1 | * | 9/2001 | Khosravi et al. | 623/1.13 |
| 2001/0047200 A1 | * | 11/2001 | White et al. | 623/1.15 |

FOREIGN PATENT DOCUMENTS

| | | |
|---|---|---|
| EP | 0852933 A2 | 7/1998 |
| JP | 2940866 | 8/1999 |
| WO | 99-49811 | 10/1997 |
| WO | 99-16387 | 4/1999 |

OTHER PUBLICATIONS

F. Khosravi, et al., PCT Publication No. WO 00/28921, "Coiled-Sheet Stent-Graft with Exo-Skeleton", May 25, 2000.

P.H. Bureister, et al., PCT Publication No. WO/95/31945, "Improved Tissue Supporting Devices", Sep. 30, 1995.

Pierre Hilaire, PCT Publication No. WO/98/58600, "Expandable Stent with Variable Thickness", Dec. 30, 1998.

Jean-Claude Sgro, EPO Publication No. 0 566 807 A1, Oct. 27, 1993.

* cited by examiner

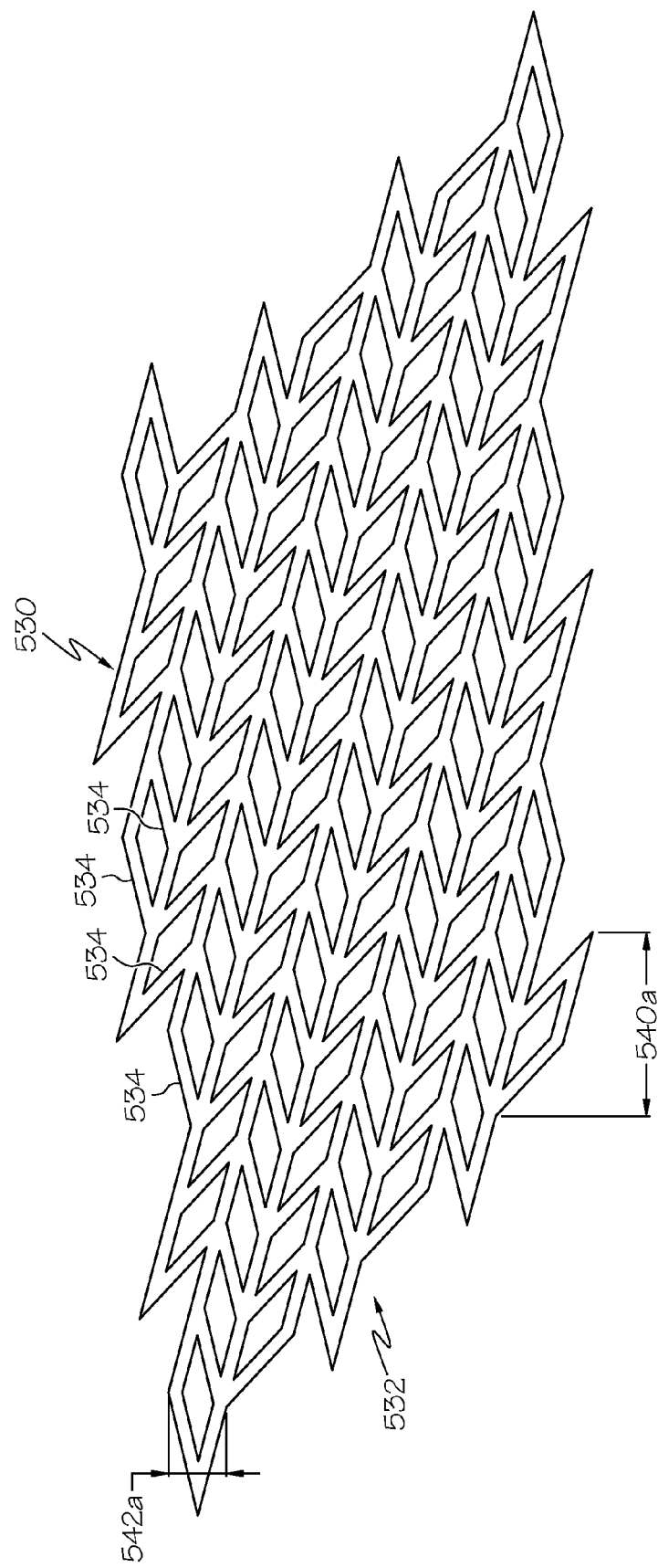

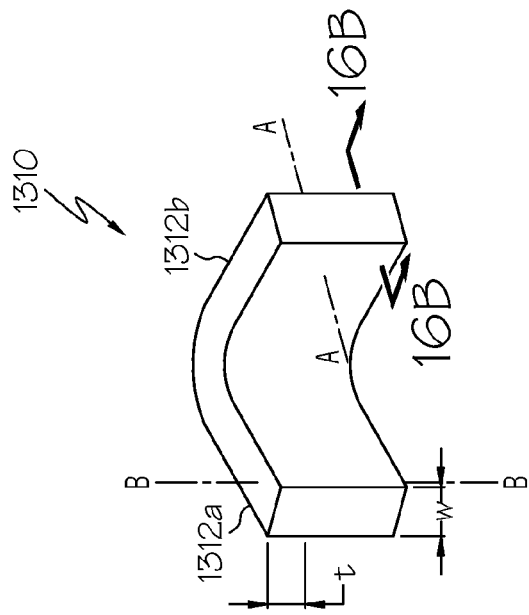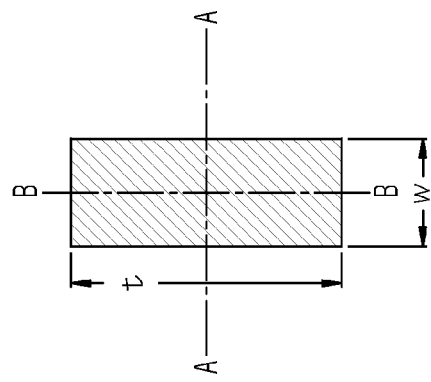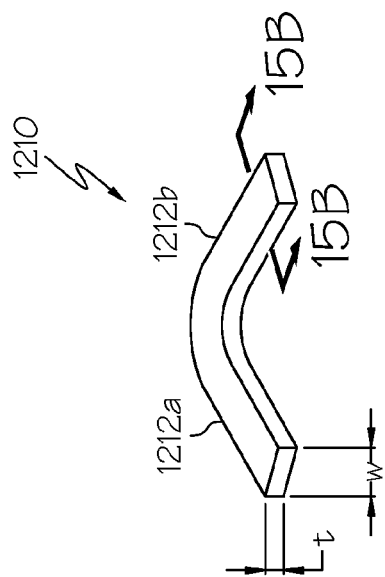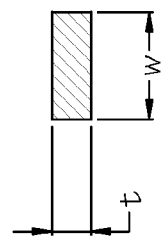

STRETCHABLE ANTI-BUCKLING COILED-SHEET STENT

This application is a Continuation-in-Part of application Ser. No. 09/192,977, filed Nov. 16, 1998 now U.S. Pat. No. 6,325,820.

FIELD OF THE INVENTION

The present invention relates generally to prostheses for implantation within body lumens, and more particularly to a coiled-sheet stent including one or more stretchable regions.

BACKGROUND

Tubular prostheses or "stents" are often implanted within blood vessels, for example, within the coronary and carotid arteries, for treating atherosclerotic disease which may involve one or more stenoses. Stents generally have a tubular shape capable of assuming a radially contracted condition to facilitate introduction into a patient's vasculature, and an enlarged condition for engaging the vessel wall at a treatment location. In its contracted condition, the stent may be placed on or in a delivery device, such as a catheter, percutaneously introduced into a patient's vasculature and advanced to a target treatment location. Once at the treatment location, the stent may be deployed and expanded to its enlarged condition, thereby engaging the wall of the vessel and substantially anchoring the stent in place.

Plastically deformable stents have been suggested that are initially provided in their contracted condition, and placed over a balloon on an angioplasty catheter. At the treatment location, the balloon is inflated to plastically deform the stent until it is expanded to its enlarged condition. Thus, the stent may be expanded to any size within a specified range to ensure that the stent substantially engages the wall of the vessel. Plastically deformable stents, however, may not expand uniformly and may not provide a desired delivery profile because of the need for a balloon on the delivery device underlying the stent.

Stents have also been suggested that are self-expanding or elastically deformable, i.e., that are biased to assume their enlarged condition but may be radially compressed to a contracted condition. The stent may be mounted on a delivery device and constrained in its contracted condition during delivery, for example, by an overlying sheath. At the treatment location, the stent may be released, for example, by retracting the overlying sheath, the stent automatically resuming its enlarged condition to engage the vessel wall. Such stents, however, may not provide as small a delivery profile as desired and may not anchor against the wall of a vessel as securely as desired, which may lead to migration of the stent within the vessel.

In addition to tubular stents, coiled-sheet stents have been suggested. A flat sheet is provided that is rolled into a spiral shape having overlapping inner and outer longitudinal sections that defines a contracted condition. The coiled-up sheet may be biased to at least partially unroll to assume an enlarged condition, and/or may be caused to unroll and radially expand using a balloon. The coiled-sheet stent may have a nondeformable lattice-like structure and a plurality of fingers or teeth along the inner longitudinal section for engaging openings in the lattice.

Once the coiled-sheet stent is deployed at the treatment location and at least partially expands, a balloon may be introduced within the stent and inflated to further expand the stent to a desired enlarged condition. When the balloon is deflated, the stent may try to radially contract, but the fingers on the inner longitudinal section may then engage corresponding openings in the lattice to lock the stent in the enlarged condition.

Coiled-sheet stents may provide enhanced anchoring within the blood vessel because the size of the fully expanded stent may be more precisely controlled. A coiled-sheet stent, however, may be more rigid transverse to its longitudinal axis than tubular stents, potentially resulting in a less flexible stent, which may not be implanted as effectively in tortuous anatomical conditions. Further, because the lattice-like structure of coiled-sheet stents is substantially nondeformable, if the stent is subjected to radially compressive forces, e.g., when the vessel wall attempts to contract, the stent may tend to buckle rather than recoil from the stress.

Accordingly, there is a need for a stent that provides improved flexibility, while still providing substantial anchoring within a blood vessel.

SUMMARY OF THE INVENTION

The present invention is directed to coiled-sheet stents having stretchable regions, preferably having programmed shape memories, and to methods for making and using such stents. In accordance with one aspect of the present invention, a stretchable stent is provided that includes a coiled-up sheet having overlapping inner and outer longitudinal sections extending generally parallel to a longitudinal axis thereof. The coiled-up sheet is expandable between a contracted condition and one or more enlarged conditions. A plurality of stretchable elements are formed in the coiled-up sheet, the stretchable elements being expandable between an unstretched condition and a stretched condition.

In a preferred form, the coiled-up sheet may be at least partially biased to expand from the contracted condition towards the one or more enlarged conditions. The stretchable elements may be biased to assume the stretched condition, thereby at least partially biasing the coiled-up sheet to radially expand from the contracted condition towards the one or more enlarged conditions.

More preferably, the coiled-up sheet may be formed from a material having a temperature-based shape memory, whereby the stretchable elements are biased towards the unstretched condition when exposed to a first temperature and towards the stretched condition when exposed to a second temperature. Preferably, the second temperature is at or above body temperature, and the first temperature is at or below about 25 degrees Celsius. Even more preferably, the coiled-up sheet is formed from Nitinol such that the Nitinol is substantially in its martensitic phase at the first temperature and substantially in its austenitic phase at the second temperature.

In alternative forms, the entire coiled-up sheet may have stretchable elements formed therein, the stretchable elements may define a longitudinal stretchable region extending between first and second ends of the coiled-up sheet and/or the stretchable elements may define a stretchable crowning end on one end of the coiled-up sheet. In the latter embodiments, the coiled-up sheet generally includes a substantially nondeformable region which may have a substantially rigid lattice-like structure. The stent may also include a plurality of locking elements extending from the inner longitudinal section for engaging openings in the outer longitudinal section to selectively secure the coiled-up sheet in the one or more enlarged conditions.

In accordance with another aspect of the present invention, a method is provided for making a coiled-sheet stent. A substantially flat sheet may be provided defining a length and a width. A plurality of stretchable elements may be formed in the sheet, the stretchable elements being expandable along the width of the sheet between an unstretched condition and a stretched condition. If desired, a plurality of locking elements may also be formed along an edge of the sheet extending along the length thereof. The stretchable elements and/or locking elements may be formed in the sheet, for example, by chemical etching, laser cutting or die punching. The flat sheet may be rolled about the width into a coiled-up sheet having overlapping inner and outer longitudinal sections, thereby providing a coiled-sheet stent having stretchable elements formed therein.

In a preferred form, the sheet is formed from a shape memory material, and at least one of the unstretched and stretched shapes is programmed into the shape memory material during the step of forming the stretchable elements. For example, the stretchable elements may be formed in the sheet in the stretched shape, and the sheet may be heat treated to program the stretched shape into the shape memory material. The stretchable elements may then be constrained in the unstretched shape after the heat treating step, for example, upon cooling the sheet after the heat treating step, and may be plastically deformed to their unstretched shape after the cooling step.

More preferably, the flat sheet is formed from Nitinol. During the heating step, the Nitinol may include austenite, and preferably the sheet is heated to a temperature of at least about body temperature, the temperature being sufficiently high such that the Nitinol substantially completes austenitic transformation. Upon cooling the sheet after the heat treating step, the Nitinol may include martensite, and preferably the sheet is cooled to a temperature of about 25 degrees Celsius or less, the temperature being sufficiently low such that the Nitinol substantially completes martensitic transformation.

In an alternative method, the stretchable elements may be formed in the sheet in their unstretched shape, and then plastically deformed to their stretched shape. The sheet may be heat treated to program the stretched shape into the shape memory material. After the heat treating step, the sheet may be cooled, thereby causing the stretchable elements to return to their unstretched shape.

The resulting coiled-sheet stent may then be used in a method for treating a patient, for example, at a target stenosis in a blood vessel, such as in the carotid or coronary arteries. A coiled-sheet stent is provided that preferably is formed from a temperature-activated shape memory material, the coiled-sheet stent including a plurality of stretchable elements having a shape memory defining an unstretched condition and a stretched condition. The stretchable elements are preferably biased to assume the stretched condition when exposed to a temperature at or above body temperature.

The coiled-sheet stent may be provided in a contracted condition on a delivery device, for example, within a distal end of a tubular sheath, at a temperature substantially below body temperature. For example, the coiled-sheet stent may be placed on a catheter which may be introduced into a lumen within the sheath, or the coiled-sheet stent may be placed within the distal end of the sheath adjacent a slidable bumper member.

The distal end of the sheath, with the stent therein, may be percutaneously introduced into a blood vessel or other body lumen of a patient, and advanced to a target treatment location. As the coiled-sheet stent becomes exposed to the body temperature within the patient during advancement, the stretchable elements become biased to assume the stretched shape due to the stent's shape memory. The stent may then be deployed, for example, by retracting the sheath while maintaining the stent at the target treatment location, the coiled-sheet stent at least partially expanding towards an enlarged condition due to the bias of the stretchable elements towards the stretched shape.

If necessary or desired, the stent may be further expanded to an enlarged condition at which the coiled-sheet substantially engages the vessel wall at the target treatment location, for example, by introducing a balloon within the deployed stent. When the balloon is deflated and withdrawn, the stent may attempt to return to its contracted condition. However, the stent preferably includes locking elements which substantially engage openings in the stent to substantially lock the stent in its enlarged condition.

The stretchable elements formed in the sheet of the coiled-sheet stent may be useful to allow recoil of the stent after implantation in a blood vessel. For example, after implantation of the stent, the blood vessel may tend to contract, thereby subjecting the stent to radially compressive forces. The stretchable elements may elastically or plastically deform from the stretched shape towards the unstretched shape to substantially reduce the risk that the stent may buckle under the compressive forces, thereby allowing the stent to partially recoil under the compressive forces.

The stretchable elements may also contribute to the initial expansion of the coiled-sheet stent upon deployment, thereby facilitating withdrawal of the delivery device, such as an underlying catheter. The combination of the bias of the stretchable elements and a bias of the coiled-sheet itself to at least partially unwind may eliminate the need for subsequent further expansion of the coiled-sheet stent, as will be appreciated by those skilled in the art.

Other objects and features of the present invention will become apparent from consideration of the following description taken in conjunction with the accompanying drawings.

BRIEF DESCRIPTION OF THE DRAWINGS

FIGS. 7A and 7B show a third preferred embodiment of an unrolled stretchable segment made of trapezoidal elements, shown in unstretched and stretched conditions, respectively.

FIGS. 15A and 15B show details of a conventional stent strut structure, in perspective and cross-sectional views, respectively.

FIGS. 16A and 16B show details of an inverted stent strut structure in accordance with the present invention, in perspective and cross-sectional views, respectively.

DETAILED DESCRIPTION OF THE PREFERRED EMBODIMENTS

Figure 1A:
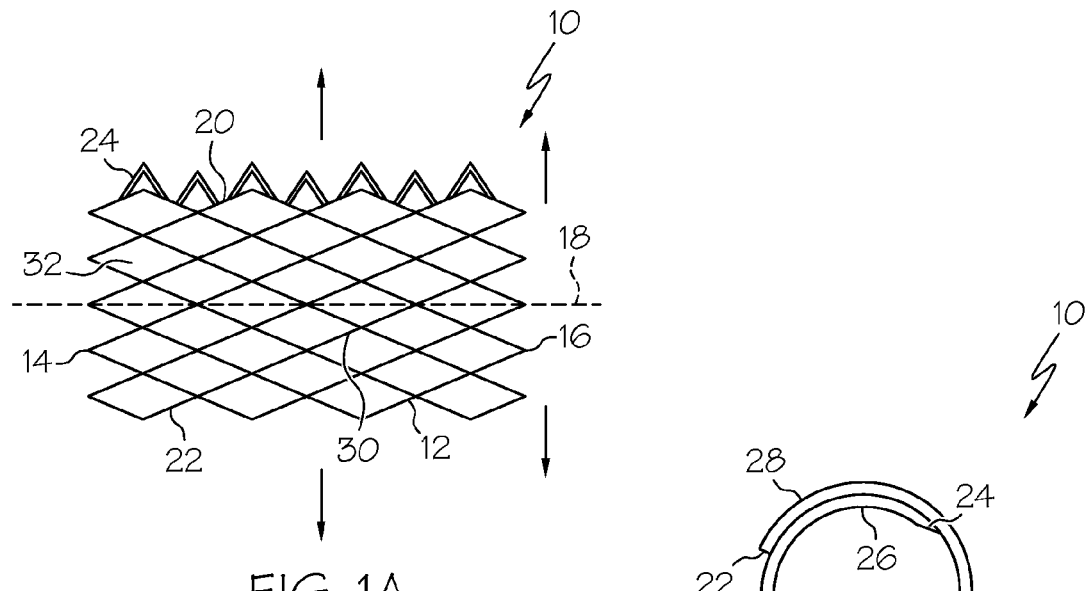
FIG. 1A is a side view of an unrolled coiled-sheet for a fully stretchable coiled-sheet stent, in accordance with one aspect of the present invention.
Figure 1B:
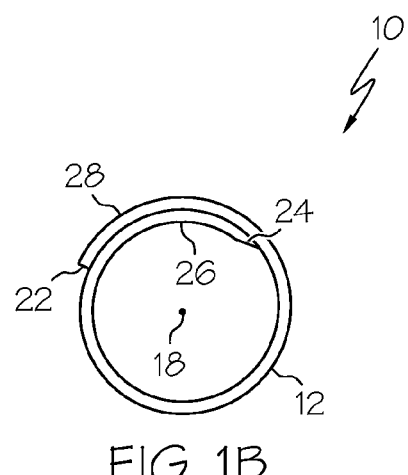
FIG. 1B is an end view of the coiled-sheet of FIG. 1A rolled into a coiled-sheet stent.

Turning now to the drawings, FIGS. 1A and 1B show a first preferred embodiment of a coiled-sheet stent 10, in accordance with one aspect of the present invention. The coiled-sheet stent 10 is formed from a substantially flat sheet 12 having first and second ends 14, 16 defining a longitudinal axis 18 therebetween. The sheet 12 also includes first and second longitudinal edges 20, 22, the first edge 20 having a plurality of fingers or teeth 24 extending therefrom substantially perpendicular to the longitudinal axis 18.

The sheet 12 also includes a plurality of stretchable elements 30 formed therein, thereby defining a multi-cellular structure capable of expanding and/or contracting in a direction substantially perpendicular to the longitudinal axis 18. Preferably, the stretchable elements 30 define a lattice-like structure providing a plurality of openings 32 for receiving the teeth 24, as described further below. The stretchable elements 30 may be elastically deformable, i.e., biased to assume a first shape but temporarily deformable from that first shape, and/or may be plastically deformable, i.e., assuming any shape to which the stretchable elements 30 are deformed.

As best seen in FIG. 1B, the sheet 12 is preferably provided in a coiled-up condition, defining overlapping inner and outer longitudinal sections 26, 28 that may slide with respect to one another to allow radial expansion of the coiled-sheet 12 between a contracted condition and one or more enlarged conditions. The coiled-up sheet 12 may be biased to the contracted condition, thereby requiring a balloon or other expandable member to radially expand the stent 10 to the enlarged condition, and/or the coiled-sheet 12 may be biased to at least partially radially expand.

In a preferred form, the stretchable elements 30 have a temperature-activated shape memory. For example, at a first temperature, the stretchable elements 30 may be biased to assume a peripherally contracted or "unstretched" shape, while at a higher second temperature, the stretchable elements 30 may become biased to assume a peripherally expanded or "stretched" shape. Preferably, the first temperature is generally about ambient temperature, such as about 25 degrees Celsius or less, and the second temperature is generally about body temperature, such as about 37 degrees Celsius or higher.

To manufacture a coiled-sheet stent 10 as described, a relatively thin, substantially flat sheet 12 is provided, for example, having a thickness of about 2-4 mm, formed from a biocompatible material, such as stainless steel or a polymer. More preferably, the sheet 12 is formed from a shape memory polymer or metal, such as a nickel-titanium alloy ("Nitinol"), more preferably having a thermally-activated shape memory. Alternatively, an elastic material, such as tantalum, platinum or tungsten alloy, or a super-elastic material, such as Nitinol, may be used. The stretchable elements 30, the teeth 24 and/or any other openings in the sheet 12 may be formed using a number of conventional metal working processes, such as die and punch, laser cutting, or chemical etching.

In one preferred method, the stretchable elements 30 are formed in their stretched shape and the sheet 12 is subsequently heat treated, for example, to a temperature of about 500 degrees Celsius or more, for a predetermined time to activate the shape memory of the material, as is known in the art. After the sheet 12 has cooled, the stretchable elements 30 are compressed into their unstretched shape, and the sheet 12 is rolled to provide a coiled-sheet stent 10.

Preferably, the sheet is formed from Nitinol which, when heat treated, is converted substantially to its austenitic phase, i.e., set to assume its stretched shape. As it is cooled, the Nitinol material preferably undergoes martensitic transformation. When the stretchable elements 30 are compressed into their unstretched shape, the material is plastically deformed substantially as martensite. More preferably, a Nitinol alloy is selected such that transformation back to austenite occurs by the time the material reaches body temperature, e.g., about 37 degrees Celsius. Thus, the stretchable elements 30 may automatically become biased to assume the stretched shape upon reaching body temperature, as explained further below.

In another preferred method, the stretchable elements 30 may be formed in their unstretched shape, and then plastically deformed to their stretched shape, e.g., while the Nitinol material is in it martensitic phase. The sheet 12 may then be heat treated, e.g., to transform the material to its austenitic phase, thereby storing the stretched shape in the material's shape memory. Upon cooling, the material will transform back to martensite, thereby returning to the unstretched shape. The sheet 12 may then be rolled into its contracted condition for placement on a delivery device (not shown).

For example, the coiled-sheet stent 10, in its contracted condition, may be placed over the distal end of a delivery catheter (not shown) having a size adapted for percutaneous introduction into a patient's vasculature. A retractable sheath (not shown) may be advanced over the distal end, thereby protecting the stent 10, preventing shifting and/or preventing premature deployment. The distal end of the catheter-sheath assembly may then be percutaneously introduced into a patient's vasculature, and advanced to a target treatment location, such as a stenosis within the carotid or coronary arteries.

As the stent 10 reaches body temperature, the temperature-activated shape memory of the material is preferably activated such that the stretchable elements 30 become biased to assume their stretched shape, e.g., when the Nitinol completes transformation back to austenite. Thus, the sheath constrains the stent 10 from at least partially expanding because of the stretching of the stretchable elements 30. Once the stent 10 is properly positioned at the treatment location, the sheath may be retracted, thereby exposing the stent 10, which may then at least partially expand radially as the stretchable elements 30 assume their stretched shape.

The catheter-sheath assembly may be withdrawn, and a balloon catheter (not shown) may be introduced into the interior of the partially expanded stent 10. Alternatively, a balloon or other expandable member (not shown) may be provided on the delivery catheter adjacent to the stent 10. The balloon may be inflated, thereby further radially expanding the stent 10. Once a desired enlarged condition is achieved, the balloon is deflated and withdrawn. Preferably, the teeth 24 on the inner longitudinal edge 20 engage a set of the openings 32 in the sheet 12, thereby substantially locking the stent 10 in its enlarged condition. Thus, the teeth 24 allow the stent 10 to be ratcheted to a number of enlarged conditions as long as the inner and outer longitudinal sections 26, 28 overlap and allow the teeth 24 to engage corresponding openings 32, as will be appreciated by those skilled in the art.

Figure 2A:
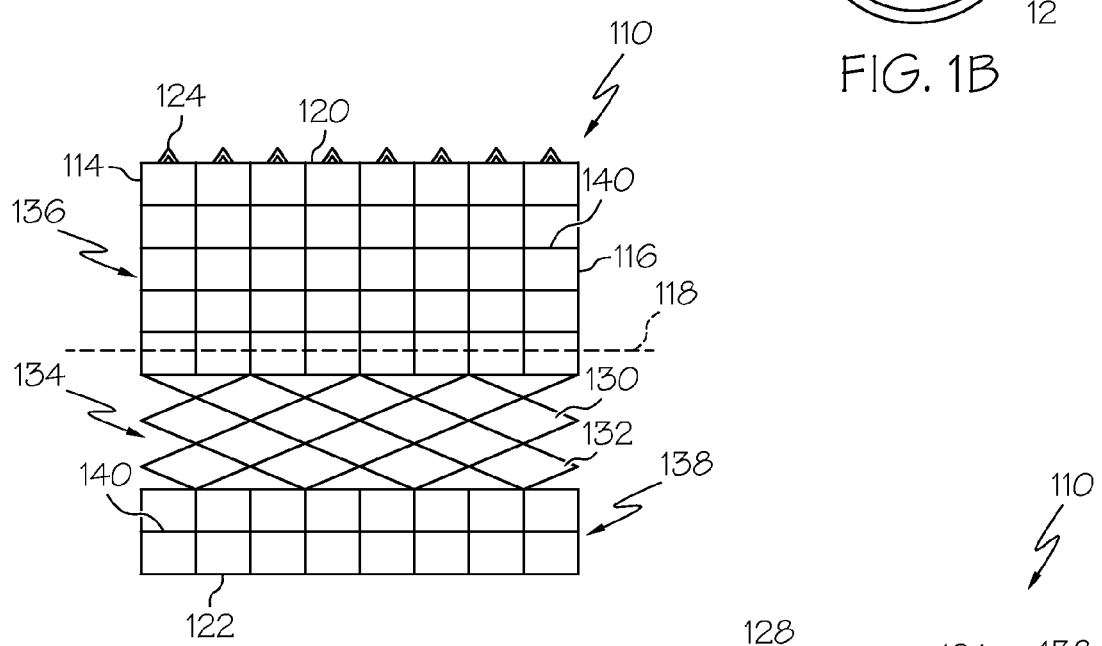
FIG. 2A is an end view of a coiled-sheet stent with a longitudinal anti-buckling region.
Figure 2B:
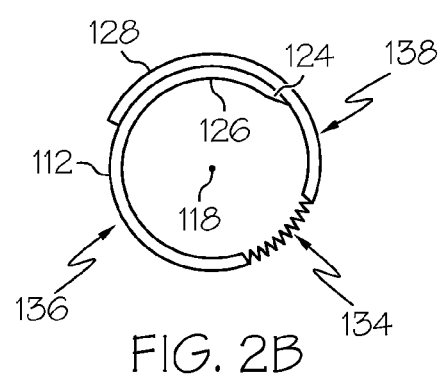
FIG. 2B is a top view of an unrolled coiled-sheet corresponding to the stent of FIG. 2A.

Turning to FIGS. 2A and 2B, a second preferred embodiment of a coiled-sheet stent 110 is shown that includes a longitudinal stretchable anti-buckling region 134. The stent 110 is formed from a sheet 112 including a plurality of stretchable elements 130, similar to the previous embodiment, that are arranged substantially parallel to the longitudinal axis 118, thereby defining the longitudinal stretchable region 134.

In addition, however, the sheet 112 includes substantially nonstretchable regions 136, 138, which preferably define a lattice-like structure formed from substantially nondeformable elements 140. For example, the thickness of the elements forming the lattice in the nonstretchable regions 136, 138 may be substantially thicker than the stretchable elements 130 in the stretchable region 134. Alternatively, the shape of the stretchable elements 130 may facilitate expansion and/or contraction perpendicular to the longitudinal axis 118. For example, in a preferred form, the lattice of the nonstretchable regions 136, 138 may be substantially rectangular, and more preferably square, to provide enhanced rigidity both parallel and perpendicular to the longitudinal axis 118.

As best seen in FIG. 2A, the sheet 12 may be rolled into the coiled-sheet stent 110, thereby providing overlapping inner and outer longitudinal sections 126, 128 such that the stretchable region 134 extends axially, i.e., substantially parallel to the longitudinal axis 118. Similar to the previous embodiment, the sheet 112 may be formed from a shape memory material, such as Nitinol, which may be stretched and heat treated, and then cooled and unstretched, or otherwise have a shape memory programmed into the material.

The longitudinal-oriented stretchable region 134 may facilitate the stent 110 partially recoiling when subjected to radially compressive forces. Once the stent 110 has been expanded and locked in an enlarged condition, the nondeformable elements 140 remain substantially rigid and will not recoil. The stretchable elements 130, however, may be compressed about the diameter of the stent 110, i.e., may be elastically or plastically deformed towards their unstretched shape when the stent 110 is subjected to radially compressive forces. Thus, the stent 110 may combine the benefits of both a coiled-sheet stent, which is generally incompressible about its diameter, and a stretchable stent structure.

Figure 3A:
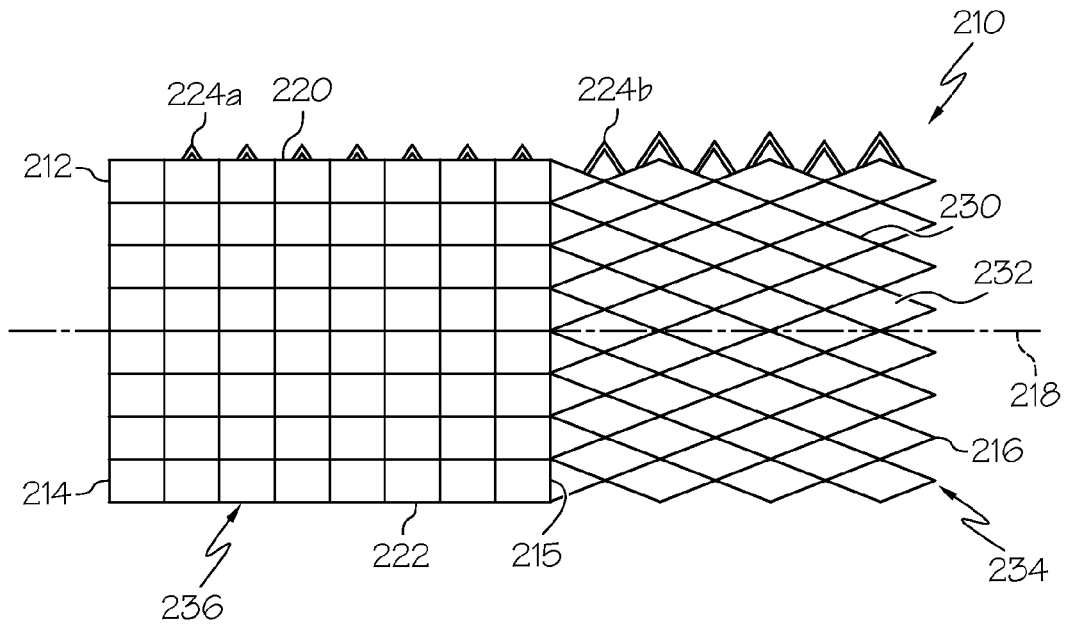
FIG. 3A is a top view of an unrolled coiled-sheet corresponding to a coiled-sheet stent having a stretchable end region.
Figure 3B:
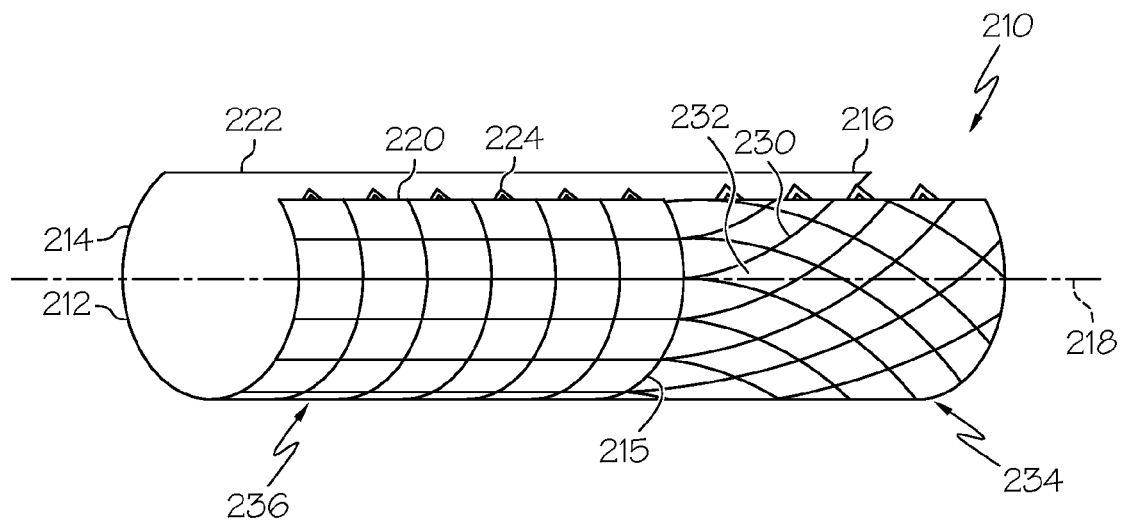
FIG. 3B is a perspective view of the coiled-sheet of FIG. 3A being rolled into a coiled-sheet stent with stretchable end region.
Figure 4A:
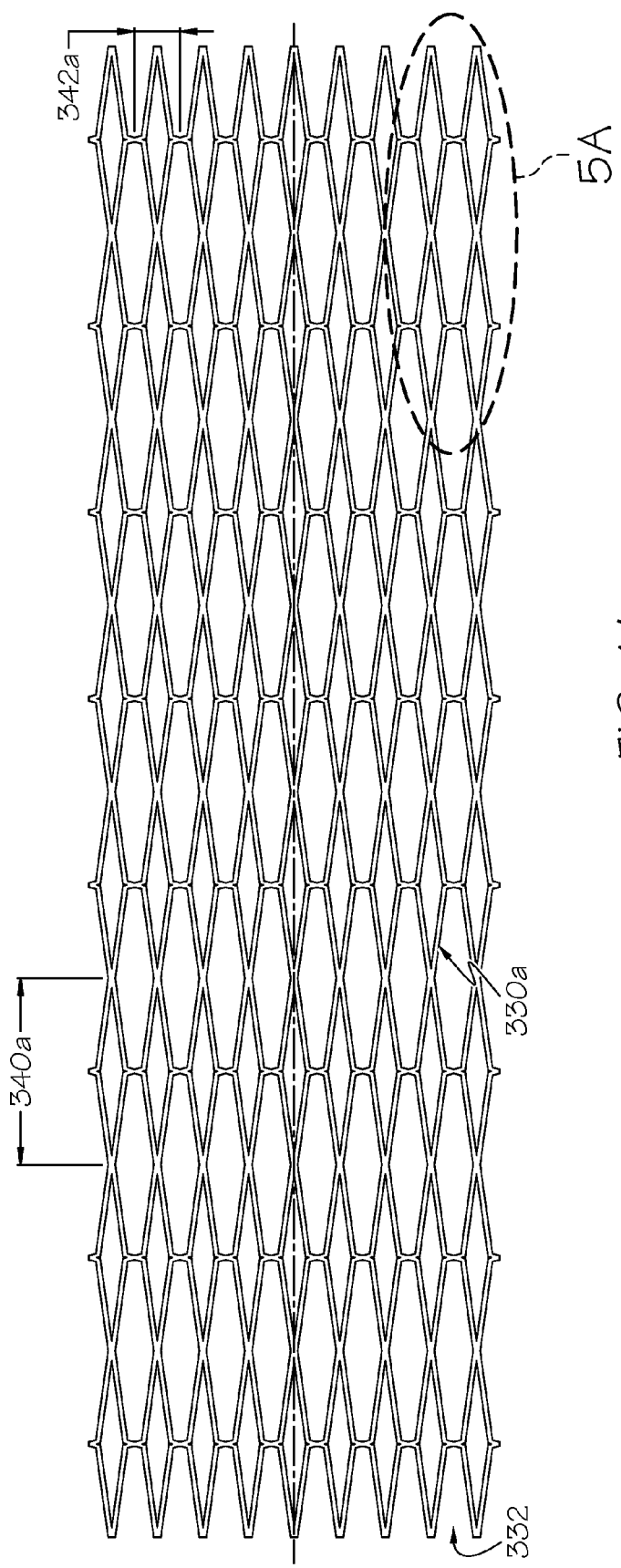
FIGS. 4A and 4B are top views of an unrolled stretchable segment of a coiled-sheet stent, showing a first preferred embodiment of a stretchable cell structure in unstretched and stretched conditions, respectively.
Figure 4B:
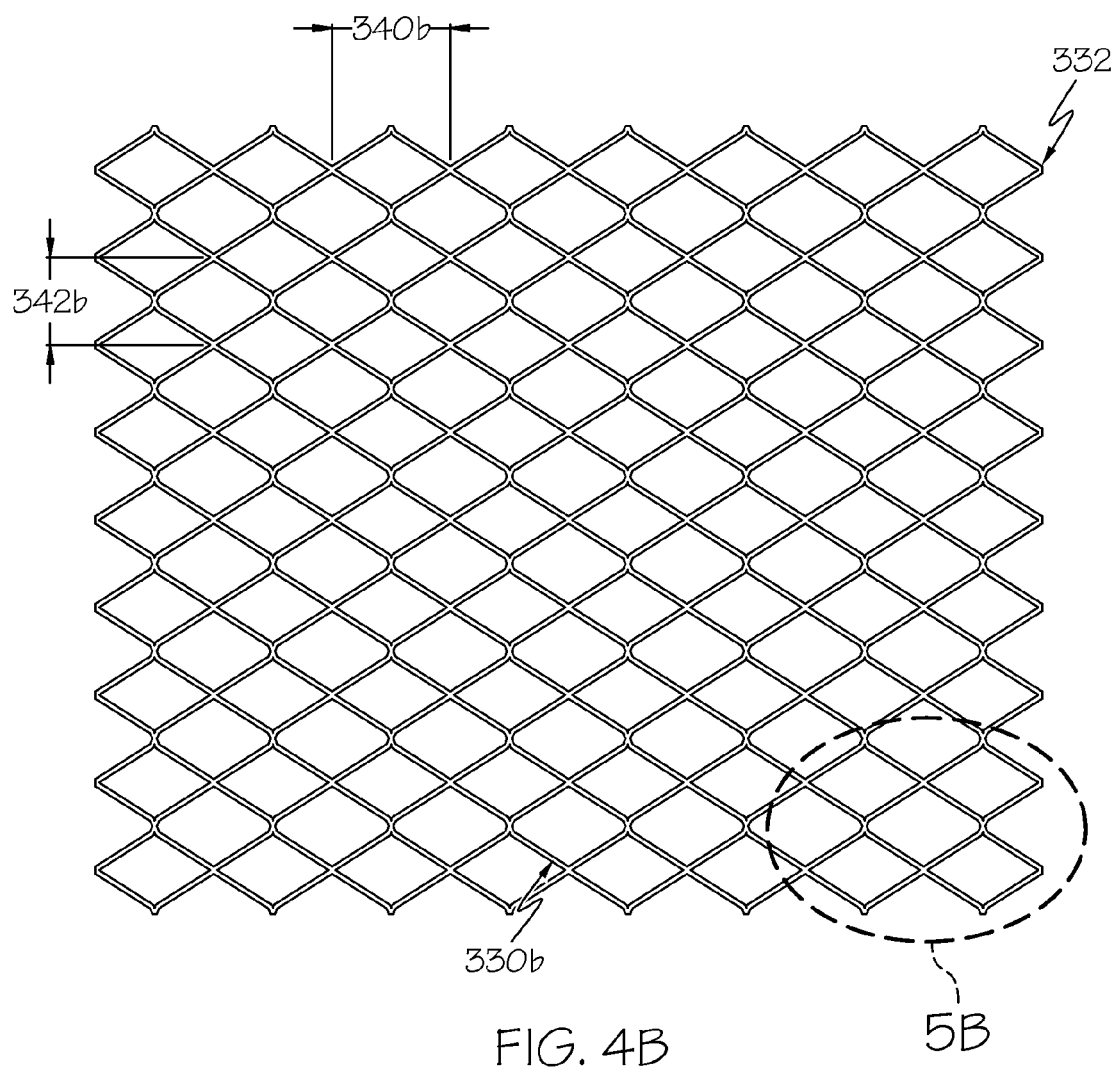

Turning to FIGS. 3A and 3B, a third preferred embodiment of a coiled-sheet stent 210 is shown that is formed from a sheet 212 including a stretchable region or "crowning end" 234 extending from one end 215 of a nondeformable region 236. Both regions 234, 236 may include teeth 224a, 224b extending from a longitudinal side edge 220 thereof, and may be rolled to define a longitudinal axis 218. The sheet 212 preferably has a shape memory, e.g., may be polished, heat treated into its stretched shape, cooled and unstretched, and then is preferably rolled into its contracted condition. When the shape memory is programmed into the sheet material, the stretchable region 234 may be shaped to assume a radially outwardly flared shape (not shown) that may facilitate anchoring of the end of the stent 210.

After the stent 210 has been implanted, the stent 210 may be subjected to radially compressive forces due to the elasticity of the vessel wall, which may cause the stretchable elements 230 in the stretchable region 234 to become compressed, similar to the embodiments described above, thereby allowing the ends of the stent 210 to partially recoil while still substantially anchoring the stent 210 in position. Alternatively, the end 216 of the stretchable region 234 may be flared outward to thereby partially recoil under radially compressive forces such that the stent adopts a substantially uniform size upon implantation within a blood vessel.

In alternative configurations, the coiled-sheet stents described herein may also include outwardly-oriented hooks or barbs (not shown) for enhancing anchoring of the stent within a body passage. Pro-thrombotic material (not shown) may be provided on the exterior surfaces of the coiled-sheet stent to enhance sealing against the wall of the body passage. Additional information on coiled-sheet stents may be found, for example, in U.S. Pat. No. 4,577,631 issued Mar. 25, 1986 in the name of Kreamer, U.S. Pat. No. 5,007,926 issued Apr. 16, 1991 in the name of Derbyshire, U.S. Pat. No. 5,158,548 issued Oct. 28, 1992 in the name of Lau et al., Re U.S. Pat. No. 34,327 reissued Jul. 27, 1993 in the name of Kreamer, U.S. Pat. No. 5,423,885 issued Jun. 13, 1995 in the name of Williams, U.S. Pat. No. 5,441,515 issued Aug. 15, 1995 in the name of Khosravi et al., and U.S. Pat. No. 5,443,500 issued Aug. 22, 1995 in the name of Sigwart. The disclosures of these references and any others cited therein are expressly incorporated herein by reference.

The stretchable elements included in the coiled-sheet stents described herein may take on a number of different forms. Generally, a plurality of stretchable elements are provided in a predetermined arrangement, such as the longitudinal or radial configurations described above, although a variety of arrangements providing a desired recoil or flexibility characteristic may be provided. Thus, each stretchable element generally comprises an individual cell, thereby providing a multi-cellular structure when the individual cells are duplicated in a predetermined pattern, as in the preferred embodiments described below. In describing these several preferred embodiments for the stretchable elements, a suffix "a" after reference numbers is used to refer to the unstretched shape, a suffix "b" is used to refer to the stretched shape, and no suffix is used when simply describing elements generally. Further, the terms "longitudinal" and "longitudinally" refer to those elements in each individual cell oriented towards the ends of the stent, i.e., arranged generally along the longitudinal axis, while the terms "peripheral" and "peripherally" refer to those elements oriented about the diameter of the stent, i.e., arranged generally perpendicular to the longitudinal axis.

Returning to the drawings, FIGS. 4A, 4B, 5A and 5B show a first preferred embodiment of a plurality of stretchable elements 330 defining a multi-cellular stretchable region 332 which may be incorporated into a coiled-sheet stent, such as those described above. Each stretchable element 330 has a generally diamond shape defined by four substantially straight segments 334 defining longitudinal apices 336 and peripheral apices 338. The straight segments 334 are generally arranged such that each stretchable element 330 has a longer longitudinal dimension or length 340 and a shorter peripheral dimension or width 342.

Figure 5A:
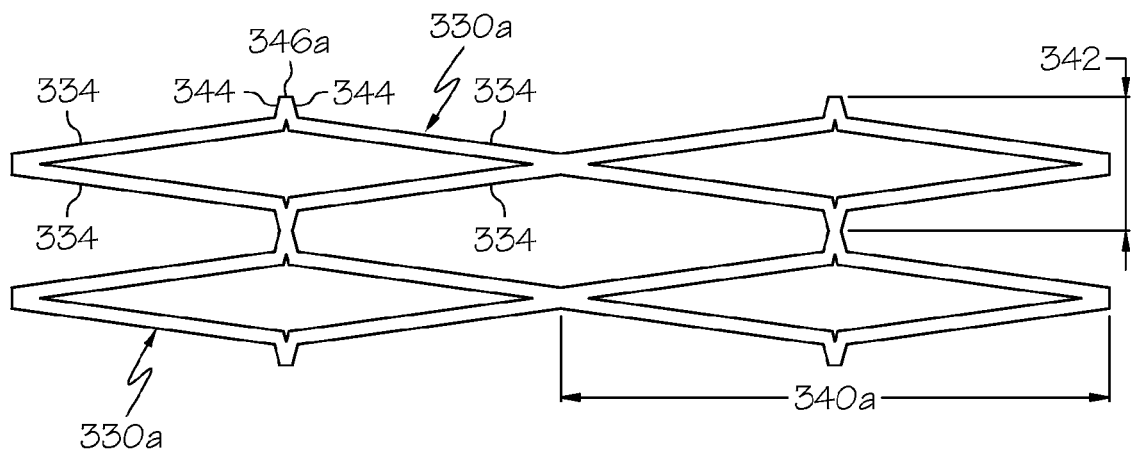
FIGS. 5A and 5B are details of the stretchable cell structure of FIGS. 4A and 4B, shown in unstretched and stretched conditions, respectively.
Figure 5B:
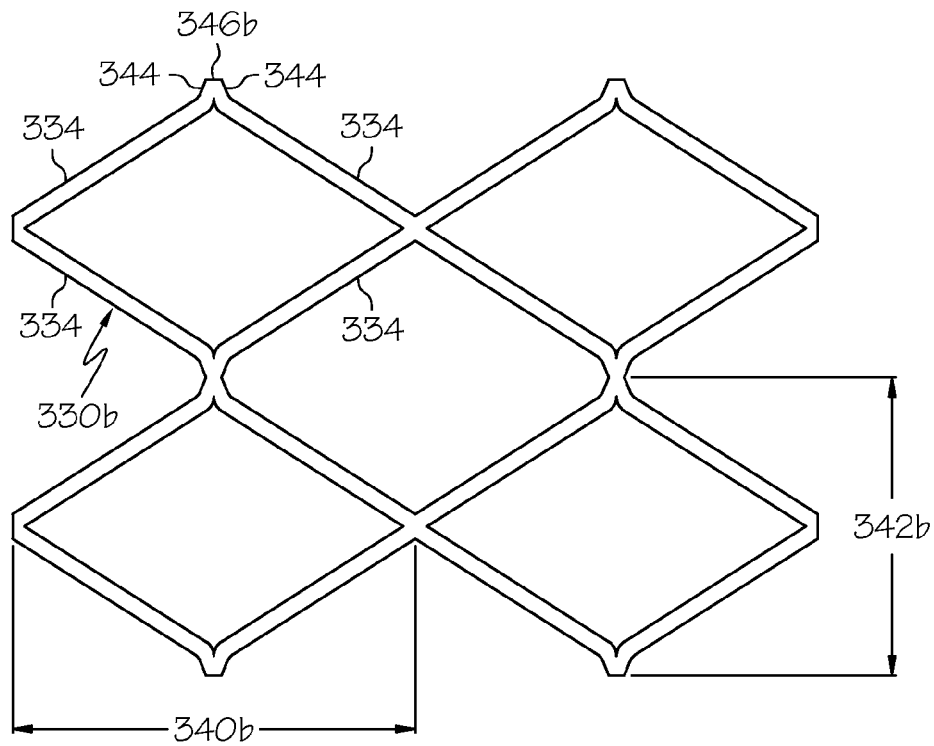

Preferably, the peripheral ends of the straight segments 334 include peripherally extending regions 344, defining a nipple-shaped region 346 at which adjacent stretchable elements 330 are connected. As best seen in FIGS. 5A and 5B, the nipple-shaped regions 346 may extend longitudinally as the stretchable elements 330 expand from their unstretched shape (FIG. 5A) to their stretched shape (FIG. 5B), thereby reducing axial foreshortening 115 of the stretchable region 332.

Because the width 342 of each stretchable element 330 is substantially smaller than the length 340, when the stretchable elements 330 expand from their unstretched shape to their stretched shape, a substantial increase in the peripheral dimension may be achieved with minimized longitudinal foreshortening. For example, in the embodiment shown, about three hundred percent peripheral expansion may be achieved with only about twelve percent foreshortening. Minimizing foreshortening may be desirable to minimize the risk of shearing along a vessel wall, which may dislodge plaque, and/or to ensure that the stent does not migrate or otherwise shift with respect to a target treatment location.

Figure 6A:
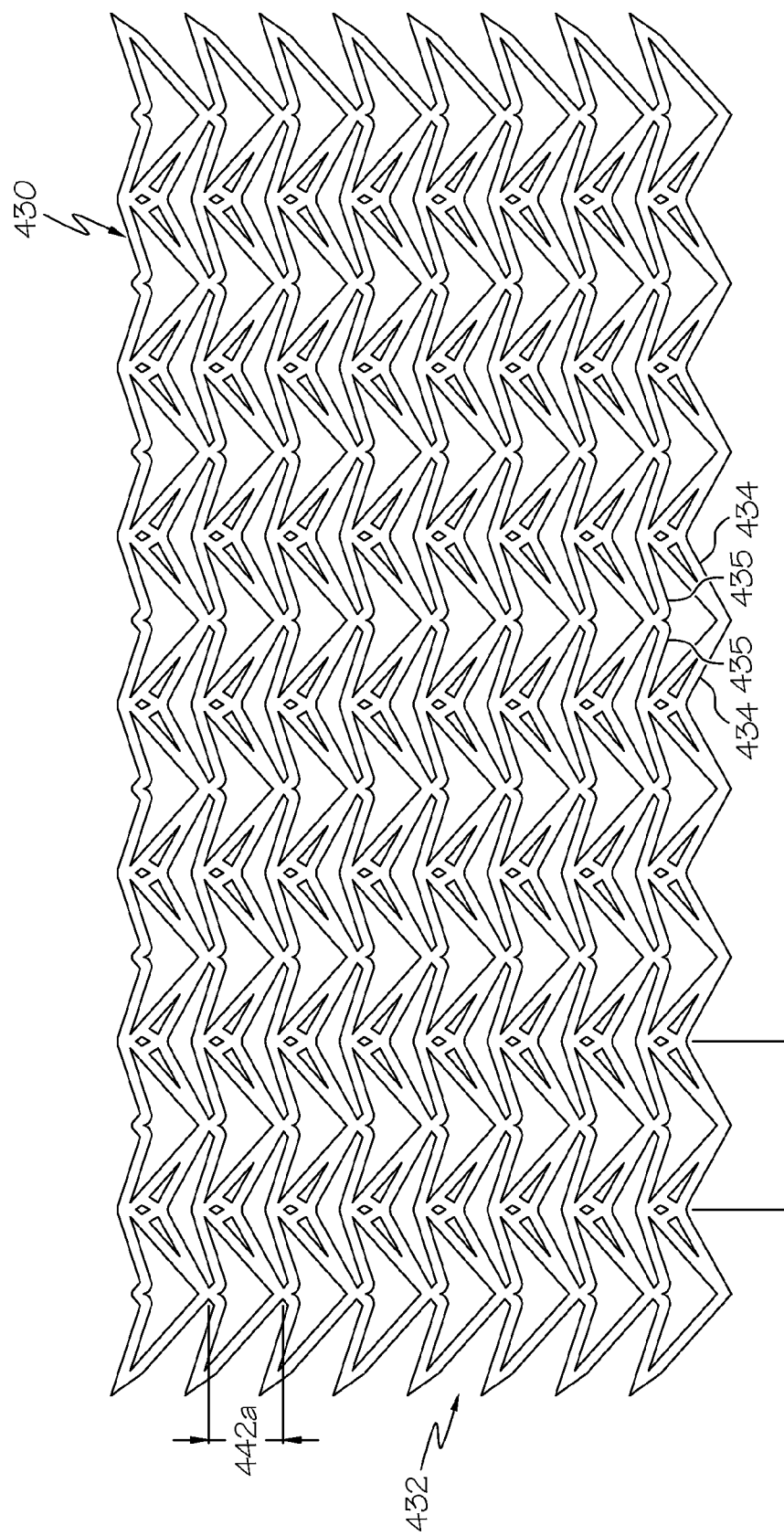
FIGS. 6A and 6B show a second preferred embodiment of an unrolled stretchable segment made of inverting elements, shown in unstretched and stretched conditions, respectively.
Figure 6B:
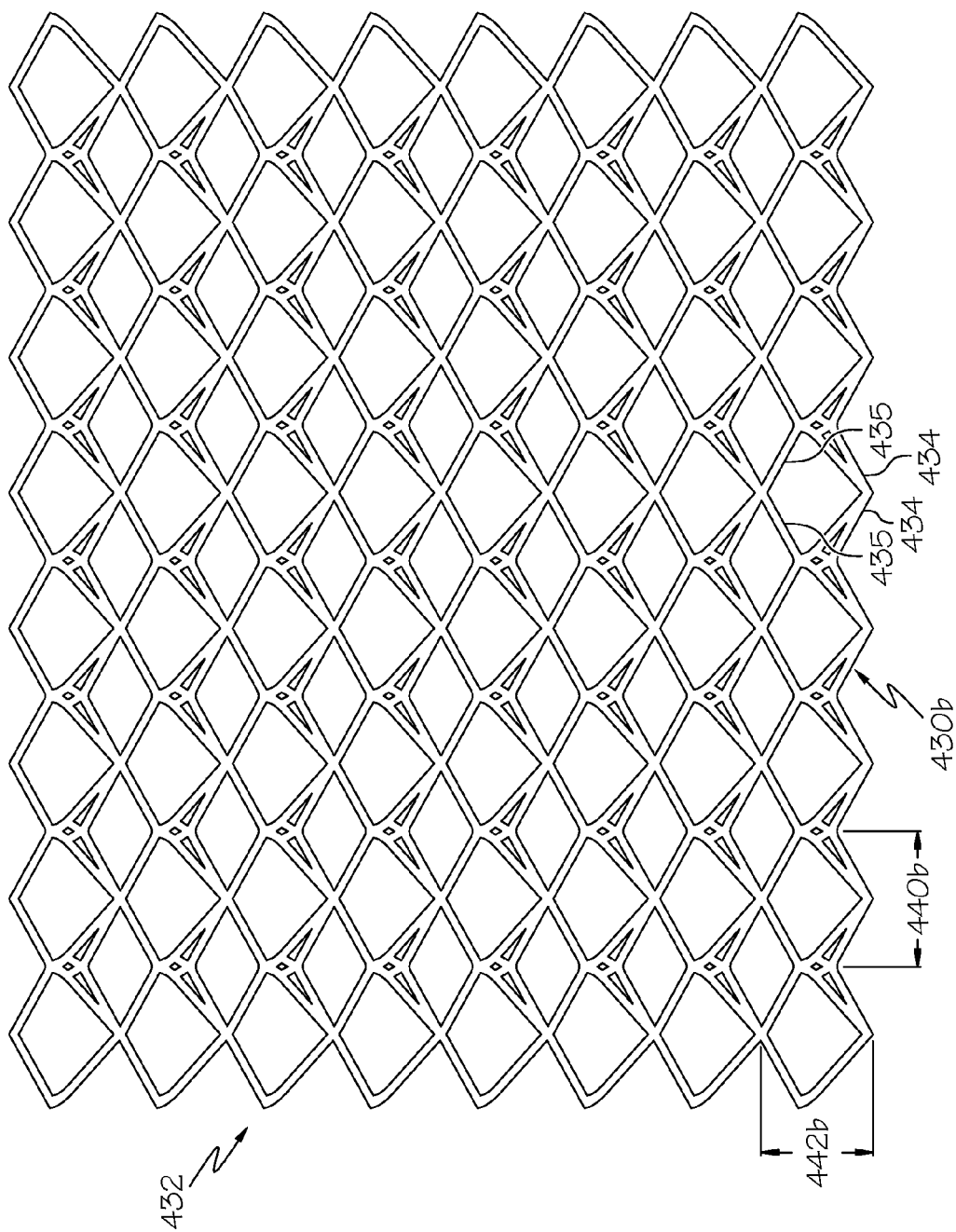

Turning to FIGS. 6A and 6B, a second preferred embodiment of a plurality of stretchable elements 430 defining a stretchable region 432 is shown. Similar to the previous embodiment, each stretchable element 430b has a generally diamond shape in its stretched shape (FIG. 6A), although, unlike the previous embodiment, each stretchable element 430a has a generally triangular or arrowhead shape in its unstretched shape (FIG. 6B). This is due to each stretchable element 430 having doubled or thicker substantially straight segments 434 on one side of the stretchable element 430 and single substantially straight segments 435 on the other side.

The shape memory is programmed into the material such that the single straight segments 435 "invert," i.e., change their orientation from being oriented generally towards the opposing double straight elements 434 in the unstretched shape to being oriented generally away from the opposing double straight elements 434 in the stretched shape. The inversion of the single straight elements 435 allows the stretchable elements 430 to expand peripherally with substantially no longitudinal foreshortening or growth. Stated differently, the width 442 of the stretchable elements 430 may increase substantially, while the length 440 of the stretchable elements 430 remains substantially constant before and after expansion.

Figure 7B:
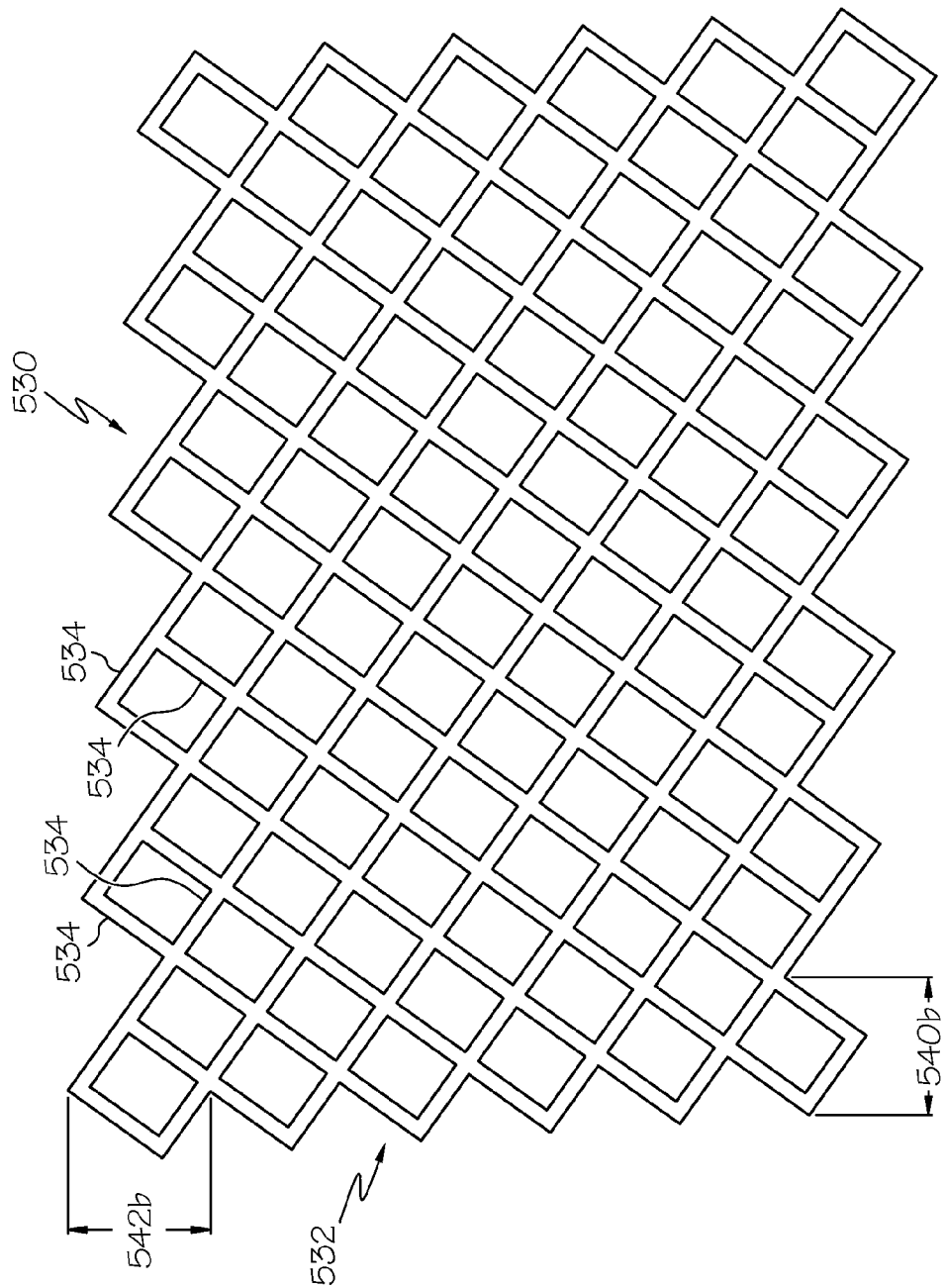

Turning to FIGS. 7A and 7B, a third preferred embodiment of a plurality of stretchable elements 530 is shown that define a stretchable region 532. The stretchable elements 530 define a generally parallelogram shape. Opposing straight segments 534 in each stretchable element 530 remain generally parallel to one another as the stretchable elements 530 are expanded from their unstretched shape (FIG. 7A) to the stretched shape (FIG. 7B). The parallelogram shape may be desirable because of its simplicity to form. If the unstretched and stretched shapes are properly selected, i.e., the length and width of the parallelogram shapes are provided in a predetermined ratio, the stretchable elements 530 may experience substantial growth in width 542 with minimal net change in length 540.

Figure 8A:
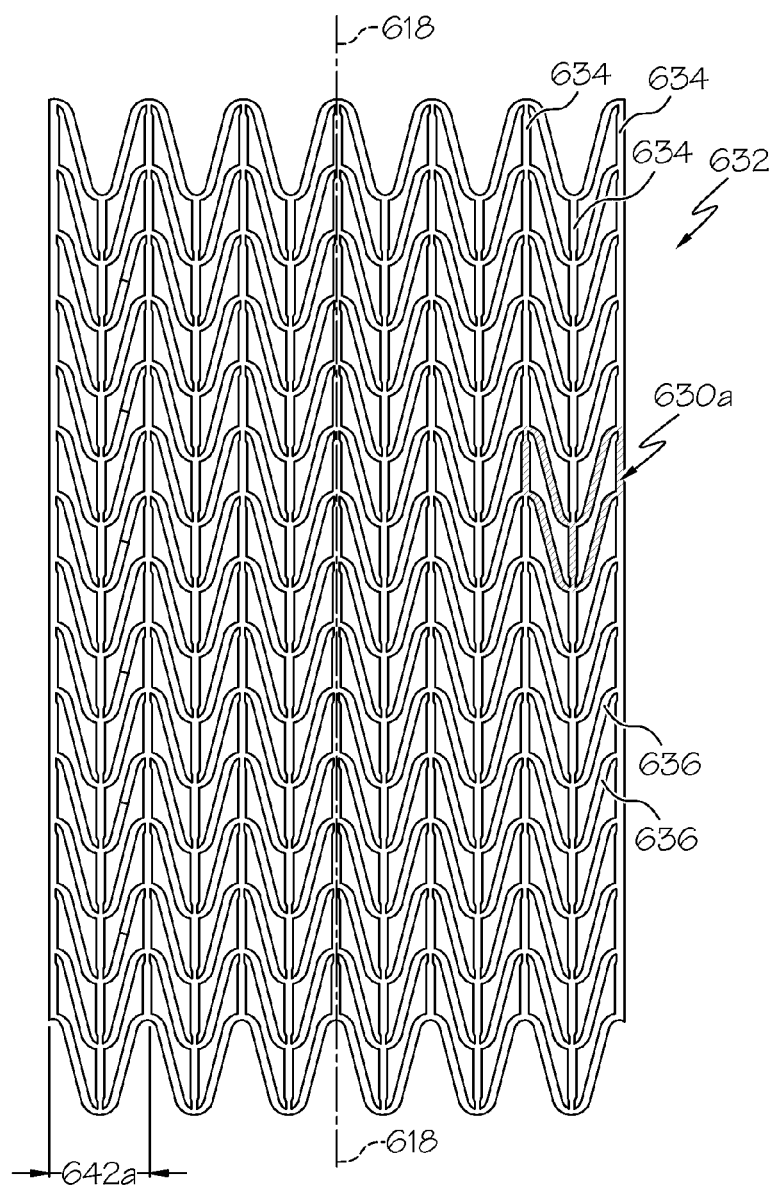
FIG. 8A shows a fourth preferred embodiment of an unrolled stretchable segment, shown in its unstretched condition.
Figure 8B:
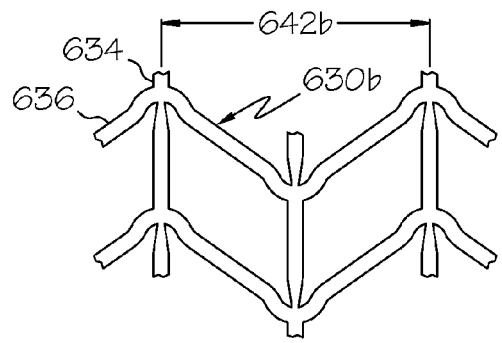
FIG. 8B is a detail of an individual stretchable element of the stretchable segment of FIG. 8A, in its stretched condition.

Turning to FIGS. 8A and 8B, a fourth preferred form of a stretchable region 632 is shown that is defined by a plurality of stretchable elements 630. A plurality of generally zigzag or sinusoidal segments 636 extend generally perpendicular to the longitudinal axis 618, and a plurality of longitudinal segments 634 extend generally parallel to a longitudinal axis 618 to connect the zigzag segments 636. The longitudinal segments 634 are preferably located at the peaks and valleys of the zigzag elements 636. Thus, each stretchable element 630 is symmetrical and is defined by opposing portions of longitudinal segments 634 and opposing portions of zigzag segments 636 with a portion of a longitudinal segment 634 extending axially therethrough at an intermediate location.

Preferably, in their unstretched shape, as shown in FIG. 8A, the zigzag segments 636a have a curved or bent configuration that minimizes the peripheral dimension or width 642a of the stretchable elements 630a. In their stretched shape, as shown in FIG. 8B, the zigzag segments 636b may substantially straighten and/or assume a more peripherally-oriented configuration, thereby substantially increasing the width 642b of the stretchable elements 630b. Thus, a desired peripheral expansion may be stored in the zigzag segments 636, while a minimal longitudinal foreshortening is encountered during expansion because of the fixed longitudinal segments 634. The change in the overall longitudinal dimension or length of the stretchable region 632 during expansion is constant no matter the length of the stretchable region, which may be desirable for relatively long stents. It occurs from the relative axial movement of adjacent longitudinal segments 634 as the stretchable elements 630 are expanded peripherally.

Figure 9:
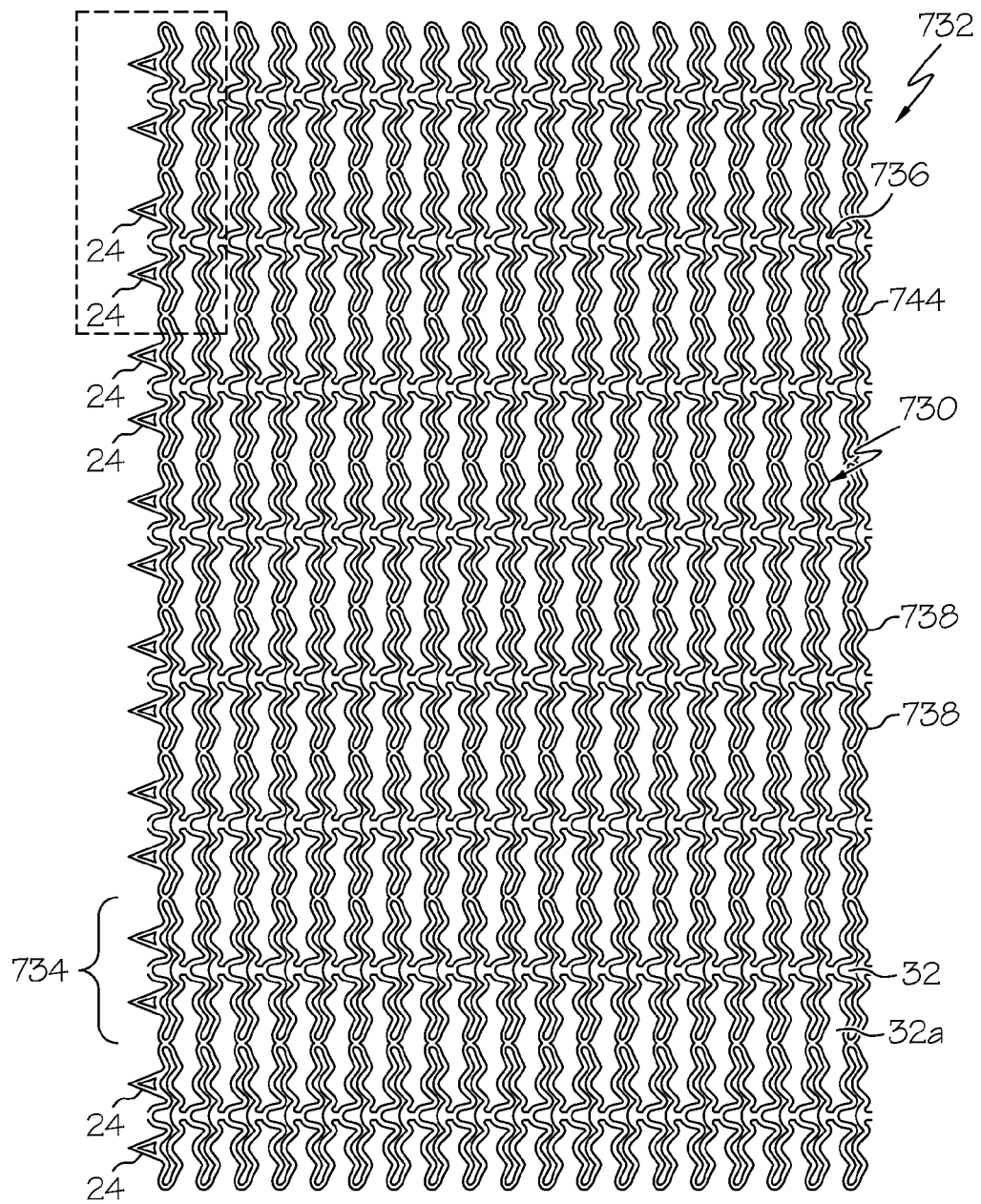
FIG. 9 shows a fifth preferred embodiment of an unrolled stretchable segment, shown in its unstretched condition.
Figure 10A:
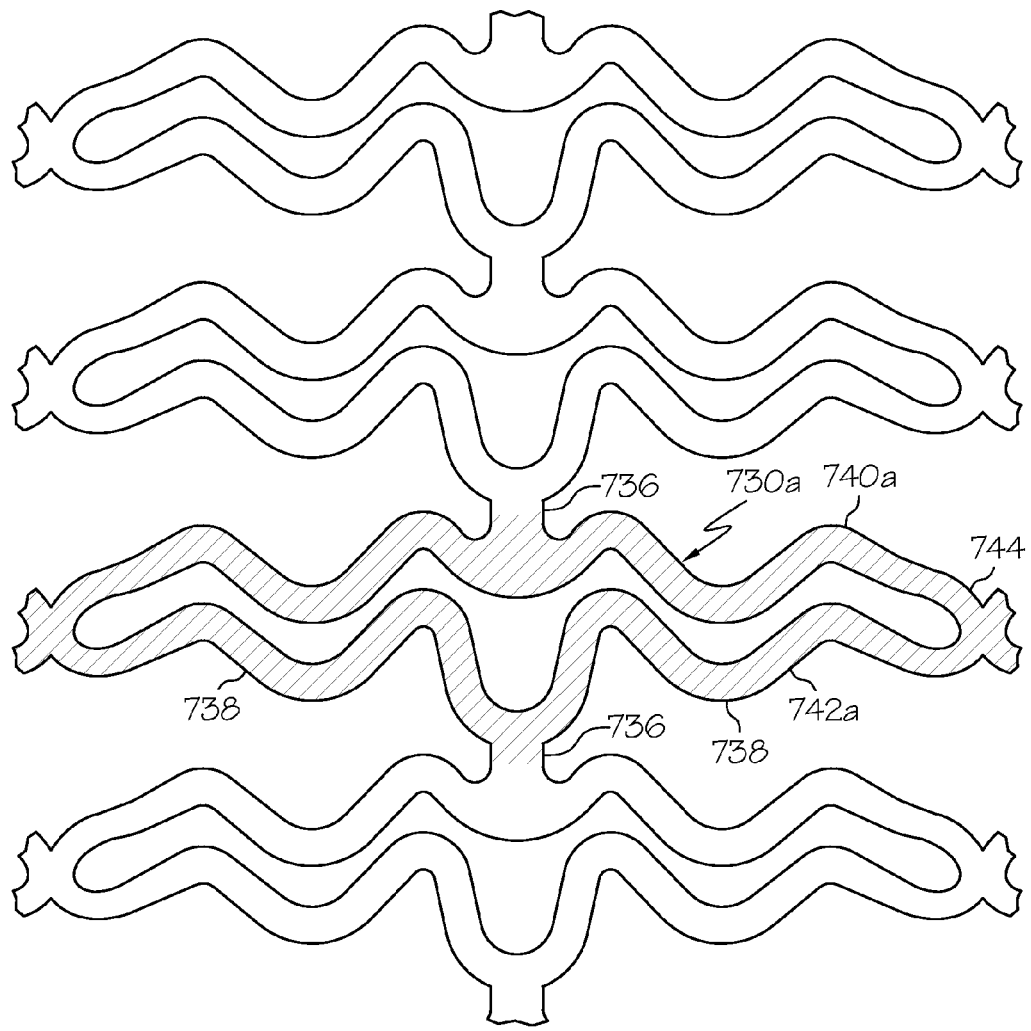
FIGS. 10A and 10B are details of the stretchable segment of FIG. 9, shown in unstretched and stretched conditions, respectively.
Figure 10B:
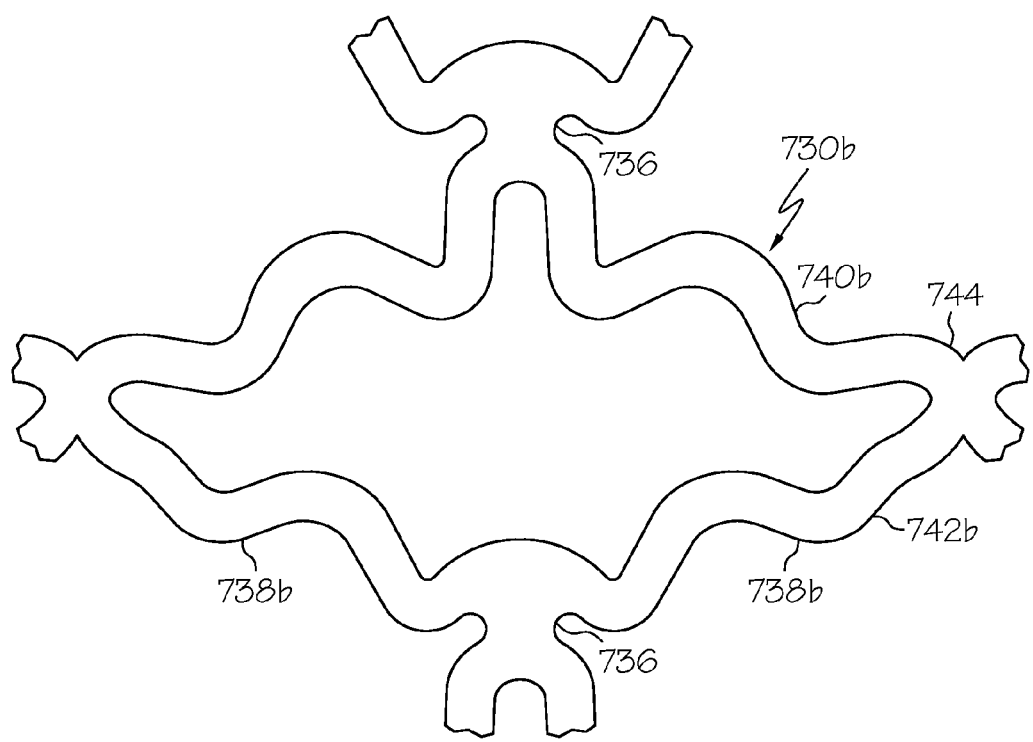

Turning to FIGS. 9, 10A and 10B, a fifth preferred embodiment of a plurality of stretchable segments 730 defining a stretchable region 732 is shown. The stretchable segments 730 are arranged in peripherally-oriented cells 734, wherein adjacent stretchable segments 730 are connected by peripheral connector elements 736. Thus, each stretchable segment 730 defines an opening or cell 32. In their unstretched shape, each stretchable element 730a is made up of a pair of longitudinal-oriented "wings" 738a. Each wing 738a includes first and second longitudinal elements 740, 742 that extend longitudinally from adjacent peripheral connector elements 736 to a looped end 744. The longitudinal elements 740, 742 preferably extend generally parallel to one another, for example, in an undulated pattern along the longitudinal axis, although alternatively, the longitudinal elements 740, 742 may be substantially straight. In FIG. 9, the undulating pattern of the longitudinal element has three turns. Stretchable elements 730 adjacent to one another in adjacent cells along the longitudinal axis 718 are preferably connected by their looped ends 744, as shown. Stretchable elements 730 which are circumferentially adjacent are connected by a peripheral connector element 736. As shown in FIG. 9, the plurality of stretchable elements 730 are positioned so that they form a plurality of quartets of stretchable elements 730. One of the plurality of quartets in FIG. 9 is indicated by a box. Note that a second opening or cell 32a is defined by two peripheral connector elements 736 and four longitudinal elements, one longitudinal element from each of the stretchable elements 730 forming the quartet. As shown in FIG. 9 the second opening or cell 32a has a larger size or larger area than the opening or cell 32 defined by the stretchable element when the stent is in its unstretched condition.

As shown in FIG. 10B, when the stretchable elements 730b are expanded to their stretched shape, the wings 738b open peripherally, i.e., the adjacent peripheral connectors 736 and the longitudinal elements 740, 742 are directed peripherally away from one another. Because of the undulated pattern in the longitudinal elements 740, 742, longitudinal foreshortening of the stretchable elements 730 may be minimized by at least partial straightening of the longitudinal elements 740b, 742b.

Figure 11:
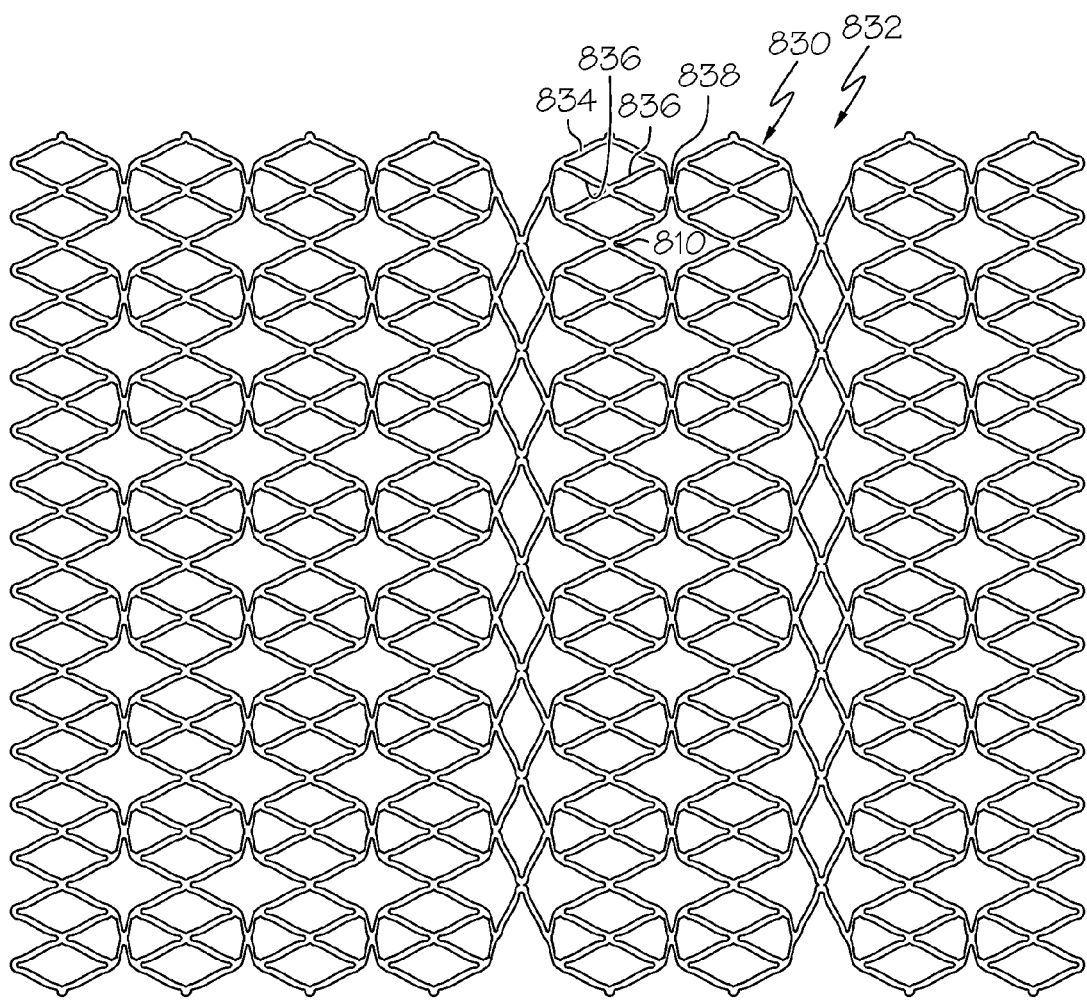
FIG. 11 shows a sixth preferred embodiment of a unrolled stretchable segment in its unstretched condition.

Turning to FIG. 11, a sixth preferred embodiment of a stretchable region 832 is shown that is defined by a plurality of stretchable elements 830 that are connected together in a predetermined pattern. Each stretchable element 830 is formed from a generally octagonal-shaped segment 834 having a pair of substantially straight cross segments 836 extending across from opposite corners. Connector elements 838, 840 connect adjacent octagonal-shaped segments 834 at the corners not connected by the crossing segments 836.

Figure 12:
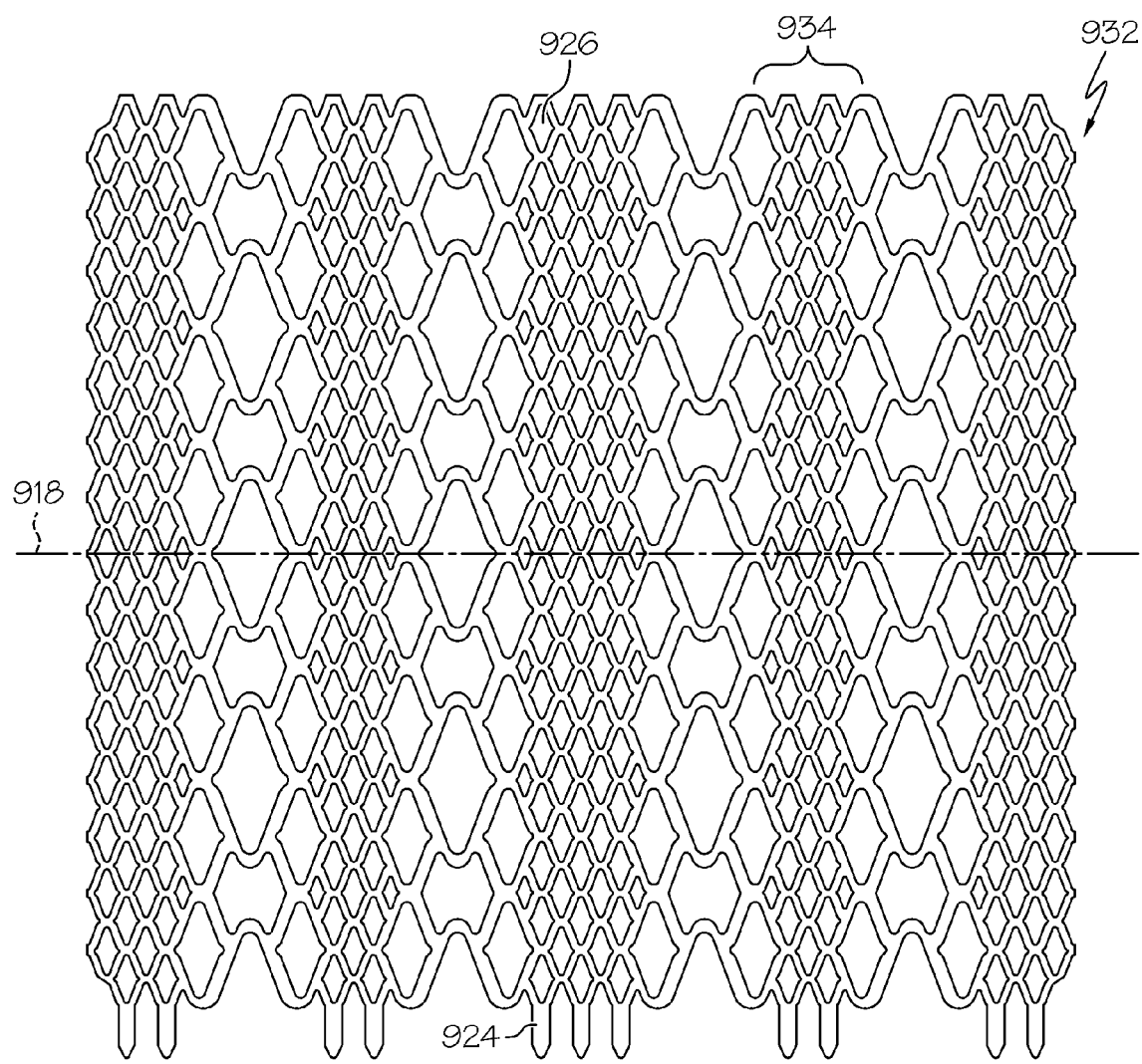
FIG. 12 shows a seventh preferred embodiment of an unrolled coiled-sheet having stretchable elements.

Turning to FIG. 12, a seventh preferred embodiment of a plurality of stretchable elements 930 formed into flat sheet 932 is shown. Each stretchable element 930 has a generally honeycomb shape, thereby defining openings 926 for receiving corresponding teeth 924 therein. The stretchable elements 930 are arranged in peripherally-oriented cells 934, with adjacent cells 934 being connected together by generally "O" shaped segments. The honeycomb structure of the stretchable elements 930 may facilitate the stretchable region 932 partially recoiling when subjected to radial forces, as will be appreciated by those skilled in the art.

Figure 13:
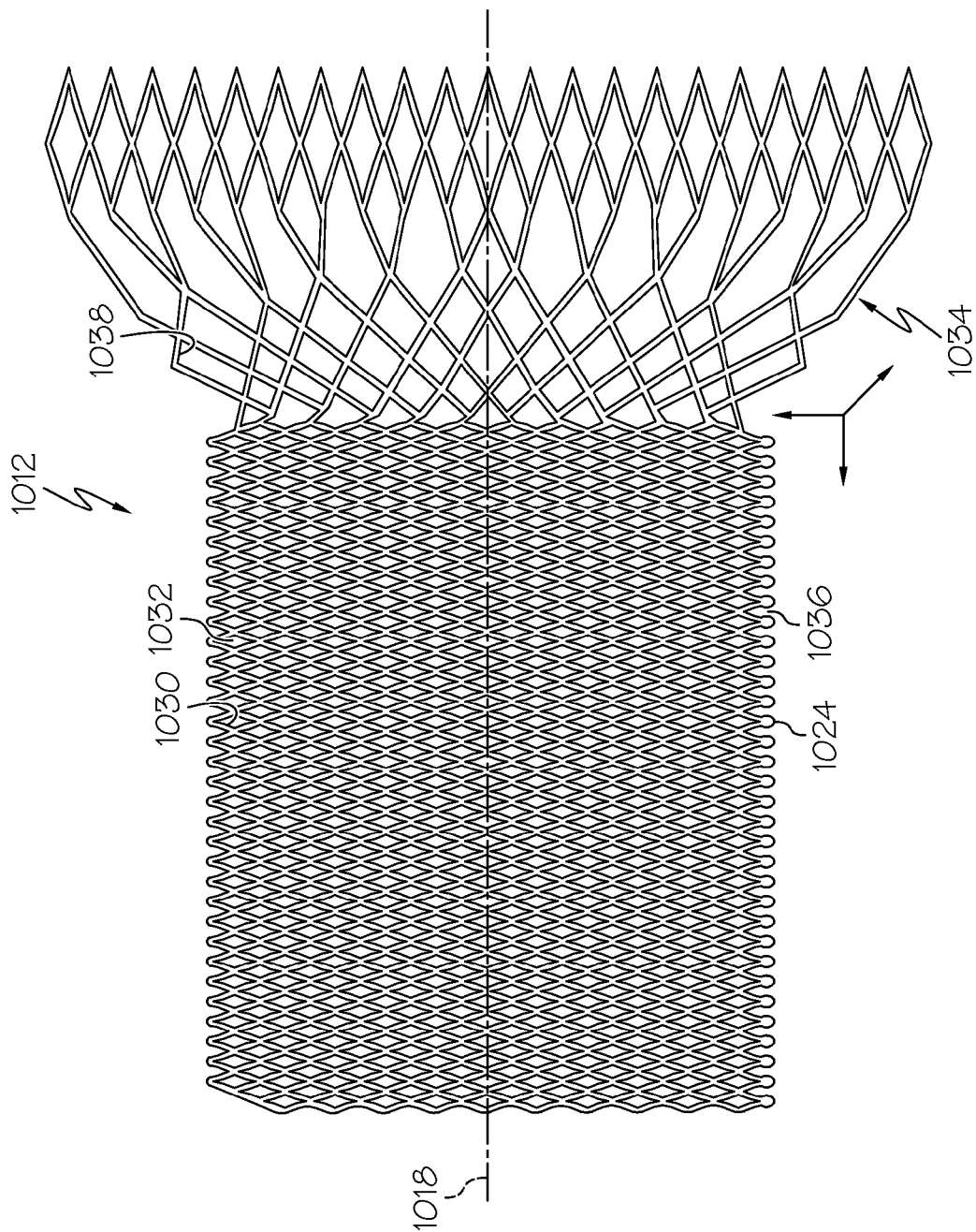
FIG. 13 is a top view of an unrolled coiled-sheet having a flared crowning end on one end of a uniform segment.

Turning to FIG. 13, another preferred embodiment of a flat sheet 1012 for a coiled-sheet stent is shown that includes a substantially nondeformable section 1036 and a stretchable section 1034. The nondeformable section 1036 is formed from a plurality of diamond-shaped elements 1030 defining openings 1032 for receiving teeth 1024 therein. The stretchable section 1034 provides a flared crowning end on the flat sheet 1012, which is formed from a plurality of diamond-shaped elements 1038. The diamond-shaped elements 1038 in the stretchable section 1034 are substantially larger and less dense than the elements 1030 in the nondeformable section 1036, thereby providing less resistance to peripheral deformation and facilitating partial recoiling of the stretchable section 1034.

Figure 14B:
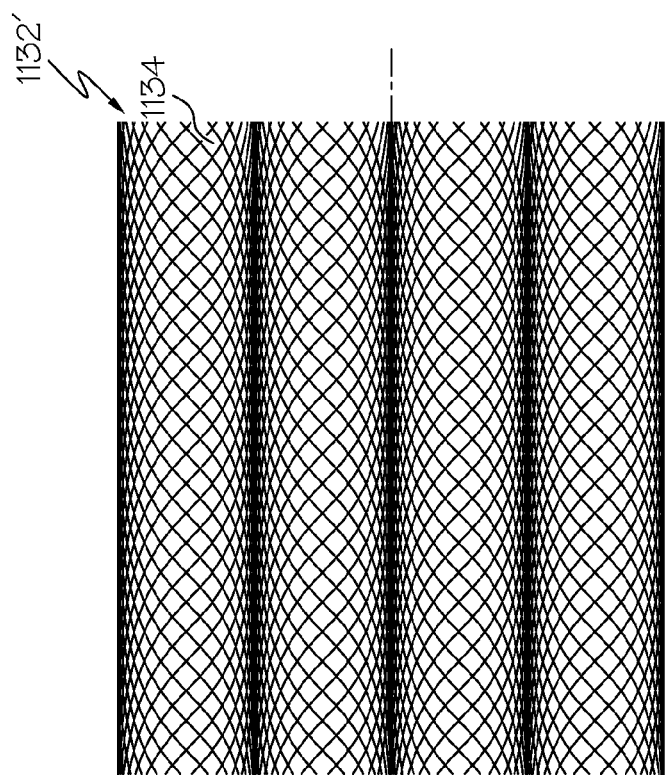
FIGS. 14A and 14B shows alternate preferred embodiments of an unrolled stretchable segment formed from interwoven sinusoidal segments.
Figure 14A:
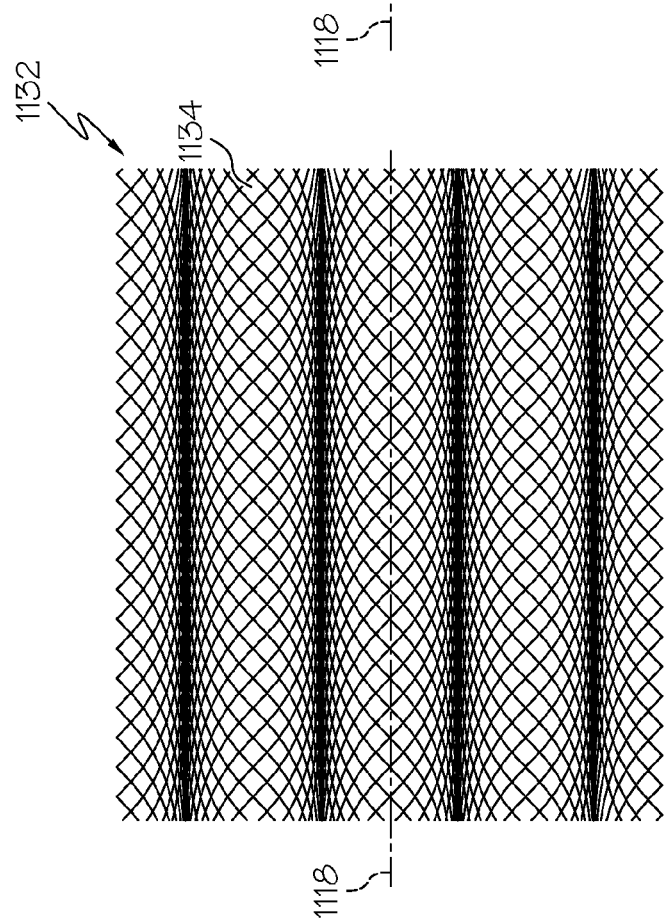

Turning to FIG. 14A, another preferred embodiment of a stretchable region 1132 is shown that is formed from a plurality of interwoven sinusoidal elements 1134. The sinusoidal elements 1134 are arranged generally parallel to the longitudinal axis 1118 and are spaced apart along the longitudinal axis from one another, thereby providing a generally diamond-shaped lattice structure. The lattice structure may facilitate partial recoil of the stretchable region 1132 when a coiled-sheet stent (not shown) formed therefrom is subjected to radial compressive forces, as previously described FIG. 14B shows a variation of FIG. 14A.

In accordance with another aspect of the present invention, a generally tubular stent is provided that includes an inverted strut structure. Generally, tubular stents have a set of struts or beams formed therein which provide the structural support for the stent. The configuration of the struts, e.g., multicellular, helical, etc., and the construction of the stent itself may provide a variety of different features. For example, a coiled-sheet stent may be desirable because of the ability to precisely control the expansion of the stent to ensure secure engagement with a vessel lumen. Plastically deformable and elastically expandable tubular stent structures are also available, which have their own advantages and disadvantages.

Generally, stents are formed from a flat or tubular sheet into which the strut structure is formed by a variety of known methods, although alternatively round or flat wires may be used to form the stent. The resulting stent is a generally tubular body expandable between a contracted condition for facilitating introduction into a body lumen, and an enlarged condition for engaging the body lumen. The tubular body has open ends defining a longitudinal axis therebetween. Struts formed in the tubular body have a width dimension extending along a periphery of the tubular body, and a thickness dimension extending radially outward substantially perpendicular to the longitudinal axis.

For reference, FIGS. 15A and 15B show a detail of a segment of a conventional stent strut structure 1210 that includes a pair of struts 1212a, b. For conventional stents, the thickness dimension "t" of individual struts 1212 is generally substantially smaller than the width dimension "w." This ratio may be considered important, for example, to minimize profile of the resulting stent to facilitate delivery and/or to minimize the protrusion of the stent, after implantation, into the lumen of the vessel, which may obstruct flow or become a source for thrombosis development.

Turning to FIGS. 16A and 16B, a detail of a segment of stent strut structure 1310 in accordance with the present invention is shown. The strut structure 1310 includes a plurality of struts 1312a, extending peripherally and/or longitudinally along all or a portion of the stent (not shown). The resulting stent may have a number of possible configurations, such as the coiled-sheet stents described above. Alternatively, tubular plastically deformable stents or stents elastically biased to expand may be provided with the features of the present invention, as will be appreciated by those skilled in the art.

The struts 1312 have a thickness dimension "t" that extends radially outward substantially perpendicular to a longitudinal axis of the stent (not shown), and a width dimension "w" that extends peripherally and/or longitudinally along the stent wall. As may be seen, the thickness dimension "t" is substantially greater than the width dimension "w." Stated differently, the ratio of width to thickness dimensions is less than one.

The "inverted" strut structure, i.e., a strut structure having a greater thickness dimension "t" than width dimension "w", has several advantages. For example, because the width dimension "w" is smaller than the thickness dimension "t," the strut structure may be more easily deformed along the periphery in order to facilitate substantially even expansion of the resulting stent. This is illustrated by reviewing the moment of inertia "I" of the strut 1312a about flexural axis A-A, which for a rectangular cross-section is defined as:

$$I_{A-A} = 1/12 w^3 t. \quad (1)$$

The moment of inertia "$I_{A-A}$" about this axis is predominated by the narrower dimension "w." The moment of inertia about the axis A-A is important because the deflection of the struts 1212 in a plane defined by the axis A-A is generally the mechanism that allows the stent to expand radially outward, as the struts deflect peripherally away from one another. Thus, the struts 1212 may provide increased flexibility as compared to conventional stent struts, which have a larger width dimension "w" than thickness dimension "t.".

In contrast, the moment of inertia "I" of the strut 1312a about flexural axis B-B may be substantially higher, as given by the following equation:

$$I_{B-B} = 1/12 t^3 w. \quad (2)$$

Because the moment of inertia "$I_{B-B}$" is predominated by the thickness dimension "t," the struts 1312 may be substantially more resistant to radial bending. Stated differently, because the moment of inertia "$I_{B-B}$" is relatively higher than conventional stent struts having the thickness dimension "t" substantially smaller than the width dimension "w," the struts 1312 minimize the likelihood of out-of-plane bending which will also ensure more even expansion of the stent within a body lumen. The increased resistance to radial deflection may also reduce recoil and/or the risk of the stent buckling under compressive forces imposed by the vessel wall after implantation.

Because of the increased thickness "t" of the struts 1312, the resulting profile of the stent, after implantation, may not be appropriate for smaller vessels, such as the coronary arteries or cerebrovascular sites. More preferably, the inverted strut structure 1310 may be used for applications within the carotid, iliac, renal and/or femoral arteries.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

What is claimed is:

1. A stretchable stent, comprising:
a coiled-up sheet having overlapping inner and outer longitudinal sections extending generally parallel to a longitudinal axis thereof, the coiled-up sheet being expandable between a contracted condition and one or more enlarged conditions, the coiled-up sheet defining a periphery in a plane substantially perpendicular to a longitudinal axis thereof;
a plurality of locking elements extending from the inner longitudinal section for engaging openings in the outer longitudinal section to selectively secure the coiled-up sheet in the one or more enlarged conditions; and
a plurality of first cells, each first cell being defined by a stretchable element formed in the coiled-up sheet and having a first area, the stretchable elements having a shape memory such that the stretchable elements are plastically deformable towards an unstretched condition at a temperature at or below about 25 degrees Celsius, and biased to expand about the periphery from the unstretched condition towards a stretched condition when exposed to a temperature at or above body temperature;
wherein each stretchable element comprises a pair of peripherally expandable wing-like elements extending generally parallel to the longitudinal axis, each pair of peripherally expandable wing-like elements comprising a first longitudinal element and a second longitudinal element, each longitudinal element being curvilinear and having three turns between a first end and a second end of the longitudinal element, the first end being engaged to a peripheral connector element and the second end being engaged to a looped end, the looped end engaging the first and second longitudinal elements;
a plurality of peripheral connector elements; and
a plurality of second cells, each second cell being defined by four longitudinal elements and two peripheral connector elements, each of the four longitudinal elements forming a portion of a different stretchable element, each second cell having a second area, the second area being greater than the first area when the stent is in the unstretched condition.

2. The stretchable stent of claim 1, wherein circumferentially adjacent stretchable elements being connected at a point intermediate the pair of wing-like elements by a peripheral connector element.

3. The stretchable stent of claim 1, wherein the turns of the first longitudinal element and the turns of the second longitudinal element are circumferentially aligned.

4. The stretchable stent of claim 1, each longitudinal element being curvilinear and having three turns between the first end and the second end of the longitudinal element when the stent is in the contracted condition and when the stent is in an enlarged condition.

5. A stretchable stent, comprising:
a coiled-up sheet having overlapping inner and outer longitudinal sections extending generally parallel to a longitudinal axis thereof, and defining a periphery, the coiled-up sheet being unrollable between a contracted condition and one or more enlarged conditions; and
a plurality of stretchable cells formed in the coiled-up sheet, each stretchable cell defining a first cell, the first cell having a first size when the stent is in the contracted condition, each stretchable cell being defined by a pair of peripherally expandable wing-like elements extending generally parallel to the longitudinal axis, each of said wing-like elements comprising first and second members that are curvilinear and have three turns between a looped end thereof, the wing-like elements being expandable about the periphery between an unstretched condition to facilitate placement in a delivery device in the contracted condition and a stretched condition to facilitate expansion of the coiled-up sheet to the one or more enlarged conditions upon deployment from the delivery device;
circumferentially adjacent stretchable cells being engaged by a peripheral connector element and longitudinally adjacent stretchable cells being engaged at their looped ends thereby forming a plurality of quartets of stretchable cells, a plurality of second cells wherein each second cell is defined by two peripheral connector elements and four curvilinear members, one curvilinear member from each stretchable cell forming one quartet of the plurality of quartets of stretchable cells, the second cell having a second size when the stent is in the contracted condition, the second size being larger than the first size.

6. The stretchable stent of claim 5, further comprising a plurality of locking elements extending from the inner longitudinal section for engaging openings in the outer longitudinal section to selectively secure the coiled-up sheet in the one or more enlarged conditions.

7. An expandable stent, the expandable stent having an unexpanded state and an expanded state, the stent comprising:
a coiled-up sheet having overlapping inner and outer longitudinal sections extending generally parallel to a longitudinal axis thereof, the coiled-up sheet being expandable between a contracted condition and one or more enlarged conditions, the coiled-up sheet defining a periphery in a plane substantially perpendicular to a longitudinal axis thereof; and
a plurality of stretchable elements formed in the coiled-up sheet, the plurality of stretchable elements defining a plurality of first cells, each of the plurality of first cells having a first area when the stent is in an unstretched condition, wherein each stretchable element comprises a pair of peripherally expandable wing-like elements extending generally parallel to the longitudinal axis, each of said wing-like elements comprising first and second members that are curvilinear and have three turns and being connected to a longitudinally adjacent wing-like element at a looped end thereof, and wherein the stretchable elements have a shape memory such that the stretchable elements are plastically deformable towards the unstretched condition at a first temperature, and biased to expand about the periphery from the unstretched condition towards a stretched condition when exposed to a temperature at or above a second temperature;
a plurality of second cells, each second cell being defined by four longitudinal elements, each longitudinal element defining the second cell forming a portion of a different stretchable element, each of the plurality of second cells having a second area when the stent is in the unstretched condition, the second area being greater than the first area.

8. The expandable stent of claim 7, further comprising:

a plurality of locking elements extending from the inner longitudinal section for engaging openings in the outer longitudinal section to selectively secure the coiled-up sheet in the one or more enlarged conditions.

9. The expandable stent of claim 7, wherein said first temperature is at or below about 25 degrees Celsius, and said second temperature is body temperature.

* * * * *